US008188270B2

(12) United States Patent
Grunenberg et al.

(10) Patent No.: US 8,188,270 B2
(45) Date of Patent: May 29, 2012

(54) POLYMORPHOUS FORM OF 5-CHLORO-N-({(5S)-2-OXO-3[4-(3-OXO-4-MORPHOLINYL)-PHENYL]-1,3-OXAZOLIDINE-5-YL}-METHYL)-2-THIOPHENE CARBOXAMIDE

(75) Inventors: Alfons Grunenberg, Dormagen (DE); Jana Lenz, Wuppertal (DE); Gerhard Arnold Braun, Köln (DE); Birgit Keil, Düsseldorf (DE); Christian R. Thomas, Wuppertal (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 971 days.

(21) Appl. No.: 12/089,095

(22) PCT Filed: Sep. 22, 2006

(86) PCT No.: PCT/EP2006/009202
§ 371 (c)(1),
(2), (4) Date: Jun. 20, 2008

(87) PCT Pub. No.: WO2007/039132
PCT Pub. Date: Apr. 12, 2007

(65) Prior Publication Data
US 2010/0152189 A1 Jun. 17, 2010

(30) Foreign Application Priority Data
Oct. 4, 2005 (DE) .......... 10 2005 047 563
Oct. 4, 2005 (DE) .......... 10 2005 047 564

(51) Int. Cl.
*C07D 413/10* (2006.01)
*A61K 31/5377* (2006.01)
(52) U.S. Cl. .................... 544/137; 514/230.8
(58) Field of Classification Search .......... 544/137; 514/230.8
See application file for complete search history.

(56) References Cited

U.S. PATENT DOCUMENTS

| | | | |
|---|---|---|---|
| 2,811,555 A | 10/1957 | Larive et al. |
| 3,279,880 A | 10/1966 | Straley et al. |
| 4,128,654 A | 12/1978 | Fugitt et al. |
| 4,250,318 A | 2/1981 | Dostert et al. |
| 4,327,725 A | 5/1982 | Cortese et al. |
| 4,500,519 A | 2/1985 | Lormeau et al. |
| 4,705,779 A | 11/1987 | Madi-Szabo et al. |
| 4,765,989 A | 8/1988 | Wong et al. |
| 4,948,801 A | 8/1990 | Carlson et al. |
| 4,977,173 A | 12/1990 | Brittelli et al. |
| 5,002,937 A | 3/1991 | Bosies et al. |
| 5,254,577 A | 10/1993 | Carlson et al. |
| 5,349,045 A | 9/1994 | Jiang |
| 5,532,255 A | 7/1996 | Raddatz et al. |
| 5,561,148 A | 10/1996 | Gante et al. |
| 5,565,571 A | 10/1996 | Barbachyn et al. |
| 5,654,428 A | 8/1997 | Barbachyn et al. |
| 5,654,435 A | 8/1997 | Barbachyn et al. |
| 5,688,792 A | 11/1997 | Barbachyn et al. |
| 5,756,732 A | 5/1998 | Barbachyn et al. |
| 5,792,765 A | 8/1998 | Riedl et al. |
| 5,801,246 A | 9/1998 | Barbachyn et al. |
| 5,827,857 A | 10/1998 | Riedl et al. |
| 5,910,504 A | 6/1999 | Hutchinson et al. |
| 5,922,708 A | 7/1999 | Riedl et al. |
| 5,929,248 A | 7/1999 | Barbachyn et al. |
| 5,935,724 A | 8/1999 | Spillman et al. |
| 5,972,947 A | 10/1999 | Tsaklakidis et al. |
| 5,977,373 A | 11/1999 | Gadwood et al. |
| 5,998,406 A | 12/1999 | Hester et al. |
| 6,069,160 A | 5/2000 | Stolle et al. |
| 6,218,413 B1 | 4/2001 | Hester et al. |
| 6,239,152 B1 | 5/2001 | Gordeev et al. |
| 6,251,869 B1 | 6/2001 | Bohanon |
| 6,265,178 B1 | 7/2001 | Martin, Jr. |
| 6,281,210 B1 | 8/2001 | Hester, Jr. |
| 6,294,201 B1 | 9/2001 | Kettelhoit et al. |
| 6,413,981 B1 | 7/2002 | Paget et al. |
| 6,458,793 B1 | 10/2002 | Warner et al. |
| 6,805,881 B1 | 10/2004 | Kanikanti et al. |
| 6,818,243 B2 | 11/2004 | Nagashima et al. |
| 7,034,017 B2 | 4/2006 | Straub et al. |
| 7,045,631 B2 | 5/2006 | Rosentreter et al. |
| 7,078,417 B2 | 7/2006 | Rosentreter et al. |
| 7,109,218 B2 | 9/2006 | Rosentreter et al. |
| 7,129,255 B2 | 10/2006 | Rosentreter et al. |
| 7,157,456 B2 | 1/2007 | Straub et al. |
| 7,351,823 B2 | 4/2008 | Berwe et al. |

(Continued)

FOREIGN PATENT DOCUMENTS
AU  744002 B2  7/1999
(Continued)

OTHER PUBLICATIONS

Roehrig, S. et al. Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor. J. Med. Chem. 48, Sep. 22, 2005, pp. 5900-5908.
Caira, M. Crystalline Polymorphism of Organic Compounds. Springer Verlag Berlin Heidelberg 198, 1998, pp. 163-208.
Hancock, B. et al. Characteristics and Significance of the Amorphous State in Pharmaceutical Systems. Journal of Pharmaceutical Science. 86, 1 (Jan. 1997), pp. 1-12.
Bono, F., et al., "Human Umbilical Vein Endothelial Cells Express High Affinity Receptors for Factor Xa", Journal of Cellular Physiology, 1997, vol. 172, pp. 36-43.
Cocks, T. M., et al., "Protease-Activated Receptors: Sentries for Inflammation", Tips, 2000, vol. 21, pp. 103-108.
Ross, R., "Atherosclerosis—An Inflammatory Disease", New England J. of Medicine, 1999, vol. 340, No. 2, pp. 115-126.

(Continued)

*Primary Examiner* — Timothy Thomas
(74) *Attorney, Agent, or Firm* — Connolly Bove Lodge & Hutz, LLP

(57) ABSTRACT

The present invention relates to a novel polymorphic form and the amorphous form of 5-chloro-N-({(5S)-2-oxo-3-[4-(3-oxo-4-morpholinyl)-phenyl]-1,3-oxazolidin-5-yl}-methyl)-2-thiophene-carboxamide, processes for their preparation, medicaments comprising these forms, and their use in the control of diseases.

5 Claims, 9 Drawing Sheets

U.S. PATENT DOCUMENTS

| | | |
|---|---|---|
| 2001/0029351 A1 | 10/2001 | Falotico et al. |
| 2001/0046987 A1 | 11/2001 | Hester et al. |
| 2003/0153610 A1 | 8/2003 | Straub et al. |
| 2003/0161882 A1 | 8/2003 | Waterman |
| 2004/0024660 A1 | 2/2004 | Ganesh et al. |
| 2004/0102450 A1 | 5/2004 | Ewing et al. |
| 2004/0162427 A1 | 8/2004 | Rosentreter et al. |
| 2004/0242660 A1 | 12/2004 | Straub et al. |
| 2005/0064006 A1 | 3/2005 | Perzborn et al. |
| 2005/0182055 A1 | 8/2005 | Berwe et al. |
| 2005/0261502 A1 | 11/2005 | Rosentreter et al. |
| 2006/0154969 A1 | 7/2006 | Rosentreter et al. |
| 2006/0258724 A1 | 11/2006 | Straub et al. |
| 2007/0026065 A1 | 2/2007 | Benke et al. |
| 2007/0149522 A1 | 6/2007 | Thomas |
| 2008/0026057 A1 | 1/2008 | Benke |
| 2008/0090815 A1 | 4/2008 | Straub et al. |
| 2008/0200674 A1 | 8/2008 | Straub et al. |

FOREIGN PATENT DOCUMENTS

| | | |
|---|---|---|
| DE | 2836305 A1 | 3/1979 |
| DE | 196 04 223 A1 | 8/1997 |
| DE | 19962924 A1 | 7/2001 |
| DE | 10129725 A1 | 1/2003 |
| DE | 10355461 A1 | 6/2005 |
| EP | 0 127 902 A2 | 12/1984 |
| EP | 0 316 594 A1 | 5/1989 |
| EP | 0 352 781 A2 | 1/1990 |
| EP | 0350002 A1 | 1/1990 |
| EP | 0 623 615 A1 | 11/1994 |
| EP | 0645376 A1 | 3/1995 |
| EP | 0 738 726 A1 | 10/1996 |
| EP | 0 785 200 A2 | 7/1997 |
| EP | 0930076 A1 | 7/1999 |
| EP | 0950386 A2 | 10/1999 |
| GB | 2140687 | 12/1984 |
| WO | WO-93/09103 A1 | 5/1993 |
| WO | WO-93/23384 A1 | 11/1993 |
| WO | WO-97/03072 A1 | 1/1997 |
| WO | WO-97/09328 A1 | 3/1997 |
| WO | WO-97/10223 A1 | 3/1997 |
| WO | WO-98/01446 A1 | 1/1998 |
| WO | WO-98/54161 A1 | 12/1998 |
| WO | WO-99/02525 A1 | 1/1999 |
| WO | WO-99/03846 A1 | 1/1999 |
| WO | WO-99/06371 A1 | 2/1999 |
| WO | WO-99/21535 A1 | 5/1999 |
| WO | WO-99/24428 A1 | 5/1999 |
| WO | WO-99/29688 A1 | 6/1999 |
| WO | WO-99/31092 A1 | 6/1999 |
| WO | WO-99/37304 A1 | 7/1999 |
| WO | WO-99/37630 A1 | 7/1999 |
| WO | WO-99/37641 A1 | 7/1999 |
| WO | WO-99/40094 A1 | 8/1999 |
| WO | WO-99/59616 A1 | 11/1999 |
| WO | WO-00/16748 A1 | 3/2000 |
| WO | WO-01/42242 | 6/2001 |
| WO | WO-01/44212 A1 | 6/2001 |
| WO | WO-01/46185 A1 | 6/2001 |
| WO | 01/47919 A1 | 7/2001 |
| WO | 01/47949 A1 | 7/2001 |
| WO | WO-02/25210 A1 | 3/2002 |
| WO | WO-02/064575 A1 | 8/2002 |
| WO | WO-02/070484 A1 | 9/2002 |
| WO | WO-02/070485 A1 | 9/2002 |
| WO | WO-02/070520 A1 | 9/2002 |
| WO | WO-02/079195 A1 | 10/2002 |
| WO | WO-02/079196 A1 | 10/2002 |
| WO | WO-03/000256 A1 | 1/2003 |
| WO | WO-03/008384 A1 | 1/2003 |
| WO | WO-03/035133 A1 | 5/2003 |
| WO | WO-03/053441 A1 | 7/2003 |
| WO | 2004/060887 A1 | 7/2004 |
| WO | 2005/068456 A1 | 7/2005 |
| WO | WO-2005/060940 A1 | 7/2005 |
| WO | WO-2006/072367 A1 | 7/2006 |
| WO | WO-2006/079474 A1 | 8/2006 |
| WO | WO-2007/036306 A1 | 4/2007 |
| WO | WO-2007/039122 A2 | 4/2007 |
| WO | WO-2007/039132 A1 | 4/2007 |
| WO | WO-2007/039134 A1 | 4/2007 |
| WO | WO-2007/042146 A1 | 4/2007 |
| WO | WO-2008/012002 A1 | 1/2008 |
| WO | WO-2008/052671 A1 | 5/2008 |

OTHER PUBLICATIONS

Nakata, M., et al., "DX9065a an Xa Inhibitor, Inhibits Prothrombin-Induced A549 Lung Adenocarcinoma Cell Proliferation", Cancer Letters, 1998, vol. 122, pp. 127-133.

Kaiser, B., et al., "A Synthetic Inhibitor of Factor Xa, DX-9065a, Reduces Proliferation of Vascular Smooth Muscle Cells in Vivo in Rats", Thrombosis Research, 2000, vol. 98, pp. 175-185.

Altieri, D. C., et al., "Identification of Effector Cell Protease Receptor-1", The Journal of Immunology, 1990, vol. 145, No. 1, pp. 246-253.

Coughlin, S. R., "Thrombin Signalling and Protease-Activated Receptors", Nature, 2000, vol. 407, pp. 258-264.

Ornstein, D. L., et al., "Cancer, Thrombosis, and Anticoagulants", Current Opinion in Pulmonary Medicine, 2000, vol. 6, pp. 301-308.

Dabbagh, K., et al., "Thrombin Stimulates Smooth Muscle Cell Procollagen Synthesis and mRNA Levels via a PAR-1 Mediated Mechanism", Thrombasis and Haemostasis, vol. 79, No. 2 1997, pp. 405-409.

Herault, J-P., et al., "Activation of Human Vascular Endothelial Cells by Factor Xa: Effect of Specific Inhibitors", Biochemical Pharmacology, 1999, vol. 57, pp. 603-610.

Leveugle, B., et al., "Heparin Oligosaccharides that Pass the Blood-Brain Barrier Inhibit β-Amyloid Precursor Protein Secretion and Heparin Binding to β-Amyloid Peptide", Journal of Neurochemistry, 1998, vol. 70, No. 2, pp. 736-744.

Molino, M., et al., "Differential Expression of Functional Protease-Activated Receptor-2 (PAR-2) in Human Vascular Smooth Muscle Cells", Arteriosclerosis, Thrombasis, and Vascular Biology, vol. 18, No. 5, 1998, pp. 825-832.

Plescia, J., et al., "Activation of MAC-1 (CD11b/CD18)-Bound Factor X by Release Cathepsin G Defines an Alternative Pathway of Leucocyte Initiation of Coagulation", Biochem. J., 1996, vol. 319, pp. 873-879.

Howells, G. L., et al., "Proteinase-Activated Receptor-2: Expression by Human Neutrophils", Journal of Cell Science, 1997, vol. 110, pp. 881-887.

Herbert, J.-M., et al., "Effector Protease Receptor 1 Mediates the Mitogenic Activity of Factor Xa for Vascular Smooth Muscle Cells in Vitro and In Vivo", J. Clin. Invest., 1998, vol. 101, No. 5, pp. 993-1000.

Donnelly, K. M., et al., "*Ancylostoma caninum* Anticoagulant Peptide Blocks Metastasis In Vivo and Inhibits Factor Xa Binding to Melanoma Cells In Vitro", Thromb Haemost, 1998, vol. 79, pp. 1041-1047.

Ragosta, M., et al., "Specific Factor Xa Inhibition Reduces Restenosis After Balloon Angioplasty of Atherosclerotic Femoral Arteries in Rabbits", Circulation, 1994, vol. 89, No. 3, pp. 1262-1271.

Zhang, Y., et al., "Tissue Factor Controls the Balance of Angiogenic and Antiangiogenic Properties of Tumor Cells in Mice", J. Clin. Invest., 1994, vol. 94, pp. 1320-1327.

Green, D., et al., "Lower Mortality in Cancer Patients Treated with Low-Molecular-Weight Versus Standard Heparin", The Lancet, 1992, vol. 339, p. 1476.

Ko, F. N., et al., "Coagulation Factor Xa Stimulates Platelet-Derived Growth Factor Release and Mitogenesis in Cultured Vascular Smooth Muscle Cells of Rat", J. Clin. Invest., 1996, vol. 98, No. 6, pp. 1493-1501.

Kakkar, A. K., et al., "Antithrombotic Therapy in Cancer", BMJ, 1999, vol. 3318, pp. 1571-1572.

Gasic, G. P., et al., "Coagulation Factors X, Xa, and Protein S as Potent Mitogens of Cultured Aortic Smooth Muscle Cells", Proc. Natl. Acad. Sci. USA, 1992, vol. 89, pp. 2317-2320.

Cirino, G., et al., "Factor Xa as an Interface Between Coagulation and Inflammation: Molecular Mimicry of Factor Xa Association with Effector Cell Protease Receptor-1 Induces Acute Inflammation In Vivo", J. Clin. Invest., 1997, vol. 99, No. 10, pp. 2446-2451.

Senden, N. H. M., et al., "Factor Xa Induces Cytokine Production and Expression of Adhesion Molecules by Human Umbilical Vein Endothelial Cells", The Journal of Immunology, 1998, vol. 161, pp. 4318-4324.

Papapetropoulos, A., et al., "Hypotension and Inflammatory Cytokine Gene Expression Triggered by Factor Xa-Nitric Oxide Signaling", Proc. Natl. Acad. Sci. USA, 1998, vol. 95, pp. 4738-4742.

Camerer, E., et al., "Tissue Factor- and Factor X-dependent Activation of Protease-Activated Receptor 2 by Factor VIIa", PNAS, 2000, vol. 97, No. 10, pp. 5255-5260.

Donovan, F. M., et al., "Thrombin Induces Apoptosis in Cultured Neurons and Astrocytes via a Pathway Requiring Tyrosine Kinase and RhaA Activities", The Journal of Neuroscience, 1997, vol. 17, No. 14, pp. 5316-5326.

Lindner, J. R., et al., "Delayed Onset of Inflammation in Protease-Activated Receptor-2-Deficient Mice", The Journal of Immunology, 2000, pp. 6504-6510.

Bouchard, B. A., et al., "Effector Cell Protease Receptor-1, a Platelet Activation-dependent Membrane Protein, Regulates Prothrombinase-catalyzed Thrombin Generation", The Journal of Biological Chemistry, 1997, vol. 272, No. 14, pp. 9244-9251.

Molino, M., et al., "Endothelial Cell Thrombin Receptors and PAR-2", The Journal of Biological Chemistry, 1997, vol. 272, No. 17, pp. 11133-11141.

Nicholson, A. C., et al., "Effector Cell Protease Receptor-1 Is a Vascular Receptor for Coagulation Factor Xa", The Journal of Biological Chemistry, 1996, vol. 271, No. 45, pp. 28407-28413.

Watson, D. J., et al., "Heparin-Binding Properties of the Amyloidogenic Peptides Aβ and Amylin", The Journal of Biological Chemistry, 1997, vol. 272, No. 50, pp. 31617-31624.

Tuszynski, G. P., et al., "Isolation and Characterization of Antistasin", The Journal of Biological Chemistry, 1987, vol. 262, No. 20, pp. 9718-9723.

Kranzhöfer, R., et al., "Thrombin Potently Stimulates Cytokine Production in Human Vascular Smooth Muscle Cells but Not in Mononuclear Phagocytes", Circulation Research, 1996, vol. 79, No. 2, pp. 286-294.

Schwartz, R. S., et al., "Neointimal Thickening After Severe Coronary Artery Injury is Limited by Short-term Administration of a Factor Xa Inhibitor", Circulation, 1996, vol. 93, No. 8, pp. 1542-1548.

Abendschein, D. R., et al., "Inhibition of Thrombin Attenuates Stenosis After Arterial Injury in Minipigs", JACC, 1996, vol. 28, No. 7, pp. 1849-1855.

Carmeliet, P., et al., "Gene Manipulation and Transfer of the Plasinogen and Coagulation System in Mice", Seminars in Thrombosis and Hemostasis, 1996, vol. 22, No. 6, pp. 525-542.

Stouffer, G. A., et al., "The Role of Secondary Growth Factor Production in Thrombin-Induced Proliferation of Vascular Smooth Muscle Cells", Seminars in Thrombosis and Hemostasis, 1998, vol. 24, No. 2, pp. 145-150.

Bevilacqua, M. P., et al., "Inducible Endothelial Functions in Inflammation and Coagulation", Seminars in Thrombosis and Hemostasis, 1987, vol. 13, No. 4, pp. 425-433.

Riedl, B., et al., "Recent Developments with Oxazolidinone Antibiotics", Exp. Opin. Ther. Patents, 1999, vol. 9, No. 5, pp. 625-633.

Barbachyn, M.R., et al., "Identification of Novel Oxazolidinone (U-100480) with Potent Antimycobacterial Activity", J. Med. Chem., 1996, vol. 39, pp. 680-685.

Tucker, J. A., et al, "Piperazinyl Oxazolidinone Antibacterial Agents Containing a Pyridine, Diazene, or Triazene Heteroaromatic Ring", J. Med. Chem. 1998, vol. 41, pp. 3727-3735.

Brickner, S.J., et al., "Synthesis and Antibacterial Activity of U-100592 and U-100766, Two Oxazolidinone Antibacterial Agents for the Potenial treatment of Multidrug-Resistant Gram-Positive Bacterial Infections" J. Med. Chem., 1996, vol. 39, pp. 673-679.

Gregory, W.A., et al., "Antibacterials. Synthesis and Structure-Activity Studies of 3-Aryl-2-oxooxazolidines. 1. The "B" Group", J. Med. Chem., 1989, vol. 32, No. 8, pp. 1673-1681.

Berry, C. N., et al., "Antithrombotic Actions of Argatroban in Rat Models of Venous, 'Mixed' and Arterial Thrombosis, and its Effects on the Tail Transection Bleeding Time", Br. J. Pharmacol., 1994, vol. 113, pp. 1209-1214.

Meng, K., et al., "Effect of Acetylsalicyclic Acid of Experimentally Induced Arterial Thrombosis in Rats", Naunyn-Schmiedeberg's Arch. Pharmacol.,1977, vol. 301, pp. 115-119.

Chern, J.W., et al., "Studies on Quinazolines IX:[1] Fluorination Versus 1,2-Migration on the Reaction of 1,3-Bifunctionalized Amino-2-Propanol with DAST", Tetrahedron Lett., 1998, vol. 39, pp. 8483-8486.

Shakespeare, W. C., et al., "Palladium-Catalyzed Coupling of Lactams with Bromobenzenes", Tetrahedron Lett., 1999, vol. 40, pp. 2035*2038.

Renger, B., et al., "Direkte N-Arylierung von Amiden: Eine Verbesserung der Goldberg-Reaktion", Synthesis, 1985, pp. 856-860.

Aebischer, E., et al., "Synthesis of N-Arylrolipram Derivatives—Potent and Selective Phosphodiesterase-IV Inhibitors—by Copper Catalyzed Lactam-Aryl Halide Coupling", Hetercycles, 1998, vol. 48, No. 11, pp. 2225-2229.

Pfeil, E., et al., "β-Aminoäthylierung von Indol und 2-methylindol", Angew Chem., 1967, vol. 79, No. 4, pp. 188-189.

Ziegler, C. B., et al., "Synthesis of Some Novel 7-Substituted Quinolonecarboxylic Acids via Nitroso and Nitrone Cycloadditions", J. Hetercycl. Chem., 1988, vol. 25, No. 2, pp. 719-723.

Bartoli, G., et al, "Electronic and Steric Effects in Nucleophilic Aromatic Substitution. Reaction by Phenoxides as Nucleophiles in Dimethyl Sulfoxide", J. Org. Chem., 1975, vol. 40, No. 7, pp. 872-874.

Reppe, et al., "N-p-Merthoxyphenyl-pyrrolidon", Justus Liebigs Ann. Chem., 1955 vol. 596, p. 208.

Luvalle, J.E., et al., "Oxidation Processes. XXI.[1] The Autoxidation of the ρ-Phenylenediamines", J. Am. Chem. Soc., 1948, vol. 70, pp. 2223-2233.

Snyder, H.R., et al., "Imidazo[4,5f]quinolines III: Antibacterial 7-Methyl-9-(substituted Arylamino)imidazo[4,5-f]quinolines", J. Pharm. Sci., 1977, vol. 66, pp. 1204-1406.

Adams, R., et al., "Sulfanilamide Derivatives. I", J. Am. Chem. Soc. 1939, vol. 61, pp. 2342-2349.

Khanna, I.K., et al., "1,2-Diarylpyrroles as Potent and Selective Inhibitors of Cyclooxygenase-2", J. Med. Chem., 1997, vol. 40, pp. 1619-1633.

Gutcait, A., et al., "Studies on Quinazolines. 6.[1] Asymmetric Synthesis of (S)-(+)- and (R)-(−)-3-[[4-(2-Methoxyphenyl)piperazin-1-yl]methylthio-2,3,-dihydromidazo[1,2-c]quinazolines", Tetrahedron Asym., 1996, vol. 7, No. 6, pp. 1641-1648.

Grell, W., et al., "Repaglinide and Related Hypoglycemic Benzoic Acid Derivatives", J. Med. Chem., 1998, vol. 41, pp. 5219-5246.

Artico, M. et al., "Rsearch on Compounds with Antiblastic Activity", Farmaco Ed. Sci. 1969, vol. 24, pp. 179-190.

Dankwardt, S. M., et al., "Nonpeptide Bradykinin Antagonist Analogs based on a Model of a Sterling-Winthrop Nonpeptide Bradykinin Antagonist Overlapped with Cyclic Hexapeptide Bradykinin Antagonist Peptides", Bioorg. Med. Chem. Lett., 1997, vol. 7, No. 14, pp. 1921-1926.

Reppe, et al., "N-6-Aminohexyl-pyrrolidon", Justus Liebigs Ann. Chem. 1955, vol. 596, pp. 204.

Bouchet, P., et al., "σ Values of N-Substitutes Azoles", J. Chem. Soc. Perkin Trans., 1974, vol. 2, pp. 449-451.

Surrey, A. R., et al., "The Preparation of N-Benzyl-3-Morpholones and N-Benzyl-3-Homomorpholones from N-(Hydroxyalkyl)-chloroacetamides" J. Amer. Chem. Soc., 1955, vol. 77, pp. 633-636.

Tong, L.K.J., et al., "The Mechanism of Dye Formation in Color Photography. VII. Intermediate Bases in the Deamination of Quinonediimines" J. Amer. Chem. Soc. 1960, vol. 82, 1988-2001.

Delande, S.A., "Heterocycles", Chemical Abstracts, American Chemical Society, 1979, vol. 90, pp. 663.

Bots, M., et al., Coagulation and Fibrinolysis Markers and Risk of Dementia, Haemostasis, vol. 28 (1998); pp. 216-222.

Benzakour, O., et al., "Cellular and molecular events in atherogenesis; basis for pharmocological and gene therapy approaches to stenosis," Cellular Pharmacology, 1996, vol. 3, pp. 7-22.
Kanthou, C., et al., "Cellular effects of thrombin and their signalling pathways," Cellular Pharmacology, vol. 2 (1995); pp. 293-302.
Kaiser, B., et al., "Antiproliferation Action of Factor Xa Inhibitors in a Rat Model of Chronic Restenosis," Abstracts of the XVIIth Congress of the International Society on Thrombosis and Haemostasis, Aug. 1999, p. 144.
Tyrrell, D., et al., "Heparin in Inflammation: Potential Therapeutic Applications Beyond Anticoagulation," Advances in Pharmacology, vol. 46 (1999); pp. 151-208.
Smirova, I., et al., "Thrombin Is an Extracellular Signal that Activates Intracellular Death Protease Pathways Inducing Apoptosis in Model Motor Neurons," J. Neurobiology, vol. 36 (1998); pp. 64-80.
Bono, F., et al., "Factor Xa Activates Endothelial Cells by a Receptor Cascade Between EPR-1 and PAR-2," Arterioscler Thromb Vasc Biol., Nov. 2000; pp. 1-6.
Lala, P. et al, "Role of Nitric Oxide in tumor progression: Lessons Learned from Experimental Tumors," Cancer and Metastasis Review, vol. 17, pp. 91-106 (1998).
Golub, T., et al., Molecular Classification of Cancer Science (1999), vol. 286, 531-537.
FDA mulls drug to slow late-stage Alzheimer's [online], [retrieved on Sep. 23, 2003]. Retrieved from the internet, URL:http://www.cnn.com/2003/HEALTH/conditions/09/24/alzheimers.drug.ap/index.html>.
Ulllman's Encyclopedia of Industrial Chemistry, Fifth Revised Ed., Editors: Elvers, B., Hawkins, S., VCH Verlagsgesellschaft mbH, Weinheim, 19985-1996, Ch. 5, 488-506.
Zhu, B., Scarborough, R., "Recent Advances in Inhibitors of Factor Xa in the Prothrombinase Complex," *Curr. Opinions Card. Pul. Ren. Inv. Drugs*, 1:63-87 (1999).
Uzan, A., "Antithrombotic Agents," *Emerging Drugs: The Prospect for Improved Medicines*, 3: 189-208 (1998).
Kaiser, B., "Thrombin and Factor Xa Inhibitors," *Drugs of the Future*, 23: 423-426 (1998).
Al-Obeidi, F., Ostrem, J., "Factor Xa Inhibitors," *Expert Opin. Therapeutic Patents*, 9: 931-953 (1999).
Al-Obeidi, F., Ostrem, J., "Factor Xa Inhibitors by Classical and Combinatorial Chemistry," *DDT*, 3: 223-231 (May 1998).
Hauptmann, J.,et al., "Synthetic Inhibitors of Thrombin and Factor Xa: From Bench to Bedside," *Thrombosis Research*, 93: 203-241 (1999).
Pschyrembel, Klinisches Worterbuch, 257. Auflage, 1994, Walter de Gruyter Verlag, p. 199-200, Stichwort "Blutgerinnung."
Rompp Lexikon Chemie, Ver. 1.5, 1998, Georg Thieme Verlag Stuttgart, Stichwort "Blutgerrinung" Lubert Stryer, Biochemie, Spektrum der Wissenschaft Verlagsgesellschaft mbH Heidelberg, 1990, p. 259.
Pschyrembel, Klinisches Worterbuch, 257. Auflage, 1994, Walter de Gruyter Verlag, p. 610, Stichwort "Heparin."
Rompp Lexikon Chemie, Ver. 1.5, 1998, Georg Thieme Verlag Stuttgart, Stichwort "Heparin."
Pschyrembel, Klinisches Worterbuch, 257. Auflage, 1994, Walter de Gruyter Verlag, p. 292, Stichwort "Cumarinderivate."
Becker, M.R., et al., "Synthesis, Sar and in Vivo Activity of Novel Thienopyridine Sulfonamide Pyrrolidininones as Factor Xa Inhibitors," *Bioorganic and Medicinal Chemistry Letters*, 9: 2753-2758 (1999).
Linder, J., et al., "Delayed Onset of Inflammation in Protease-Activated Receptor-2-Deficient Mice," J. Immunology, 2000, pp. 6504-6510.
Cirino, G. et al. Inflammation-Coagulation Network: Are Serine Protease receptors the knot?; Tips; 200, vol. 21, pp. 170-172.
Chiou, W.L. et al. Pharmaceutical Applications of Solid Dispersion Systems. Journal of Pharmaceutical Sciences 60, (1971). 128-1302.
Ford, J.L. The Current Status of Solid Dispersions. Pharm Acta Helv. 61, (1986)69-88.
Rasenack, N. et al. Poorly Water-soluble Drugs for Oral Delivery—A Challenge for Pharmaceutical Development. Pharmazeutische Industrie 67, Nr. 5 (2005), 583-591.
Breitenbach, J. Melt extrusion: from process to drug delivery technology. European Journal of Pharmaceutics and Biopharmaceutics 54 (2002) 107-117.
Breitenbach, J. Feste Loesungen durch Schmelzextrusion—ein integriertes Herstellkonzept. Pharmazie in unserer Zeit 29 (2000), 46-49.
Gilligan, D.M. et al. The Management of Atrial Fibrillation. The American Journal of Medicine, vol. 101, (4) 1996, 413-421.
Kubitza, D. et al. Novel factor Xa inhibitors for prevention and treatment of thromboembolic diseases. Expert Opinion on Investig. Drugs, vol. 15, (8) 2006, pp. 843-855.
Sinha, U. et al. Antithrombotic and hemostatic capacity of factor Xa versus thrombin inhibitors in models of venous and arteriovenous thrombosis. European Journal of Pharmacology 2000, 395, 51-59.
Betz, A. Recent advances in Factor Xa inhibitors, Expert Opinion Ther. Patents 2001, 11(6), 1007-1017.
Tan, K.T. et al. Factor X inhibitors. Expert Opinion on Investig. Drugs 2003,12, 799-804.
Ruef, J. et al. New antithrombotic drugs on the horizon. Expert Opinion on Investig. Drugs 2003, 12, 781-797.
Samama, M.M. Synthetic direct and indirect factor Xa inhibitors. Thrombosis Research 2002, 106, V267-V273.
Quan, M.L. The race to an orally active Factor Xa inhibitor: Recent advances. Current Opinion in Drug Discovery & Development 2004, 7, 460-469.
The Ephesus Study, Blood 2000, 96, 490a.
The Penthifra Study, Blood 2000, 96, 490a.
The Pentamaks Study, Blood 2000, 96, 490a-491a.
Leadley, R.J. Coagulation Factor Xa Inhibition: Biological Background and Rationale. Current Topics in Medicinal Chemistry 2001, 1, 151-159.
The Penthathlon 2000 Study, Blood 2000, 96, 491a.
Williams, E.M. Vaughan. Classificating anti-arrhythimic drugs. In: Cardiac Arrythias—Proceedings of a symposium, sandoe E., soedertaeje: Astra (1970), pp. 449-469.
http://familydoctor.org/online/famdocen/home/common/heartdisease/basics/290.html.
Kubitza, et al., Multiple dose escalation study Investigating the pharmacodyanamics, safety, and pharmacokinetics of BAY 59-7939 an oral, direct Factor Xa inhibitor in healthy male subjects, Blood, vol. 102:11:Nov. 16, 2003, p. 811a.
Kubitza, et al., Abstract 3010, Single dose escalation study investigating the pharmacodyanamlcs, safety, and pharmacokinetics of BAY 59-7939 an oral, direct Factor Xa inhibitor in healthy male subjects, Blood, vol. 102:11. Nov. 16, 2003, p. 813a.
Lerk, et al., Effect of Hydrophilization Drugs on Release Rat from Capsules, J. of Pharma. Sciences, 67(7), pp. 935-939 (1978).
Lerk, et al., In Vitro and In Vivo Availability of Hydrophilized Phenytoin from Capsules, J. of Pharma. Sciences, 68(5), pp. 634-638 (1979).
Greaves, et al., Novel Approaches to the Preparation of Low-Dose Solid Dosage Forms,Pharmaceutical Technology. Jan. 1995, pp. 60-64.
[Database Bielstein] Bielstein Institute for Organic Chemistry, Frankfurt-Main, DE. Database Accession No. 8822985.
Brittain, Harry G. (editor), "Polymorphism in Pharmaceutical Solids," publisher Marcel Dekker, Inc., New York, New York 1999, pp. 235-236.
Rouhi, Maureen A., "The Right Stuff. From Research and Development to the Clinic, Getting Drug Crystals Right is Full of Pitfalls," Science & Technology, 2003, vol. 81, No. 8, pp. 32-35.
Jain, N.K. et al., "Polymorphism in Pharmacy", Indian Drugs, 1986, vol. 23, No. 6, pp. 315-329.

Fig. 1
DSC (solid line) and TGA thermograms (dashed line)
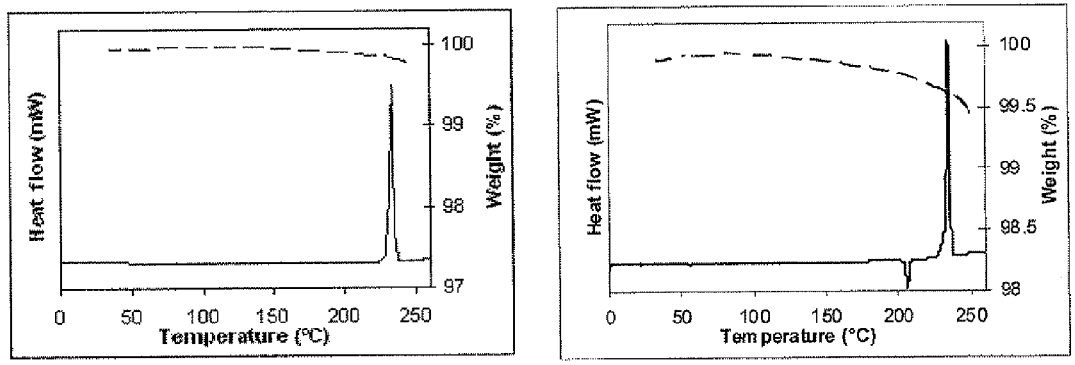
Modification I                    Modification II
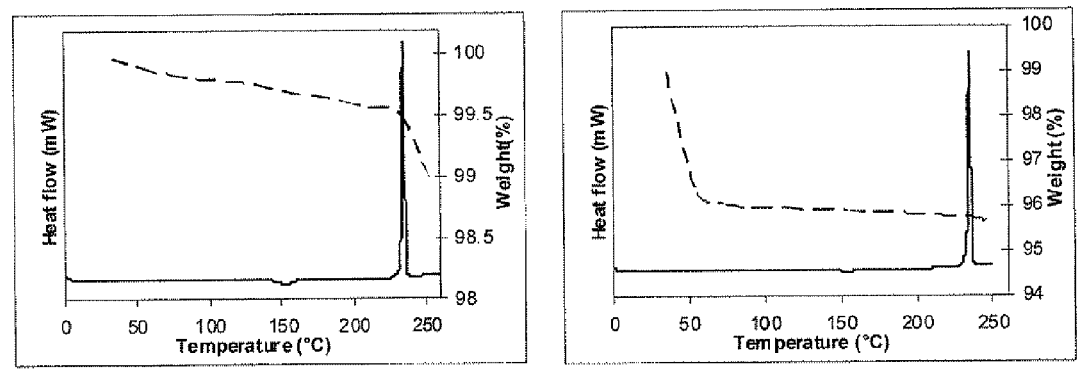
Modification III                  Hydrate
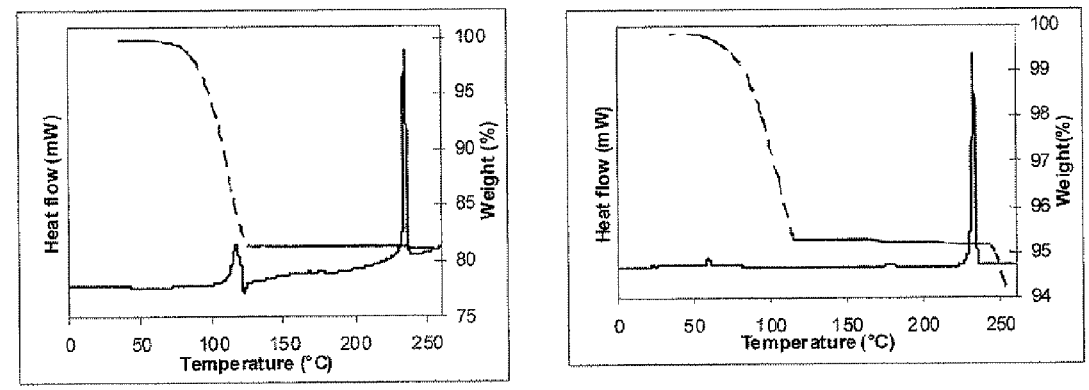
NMP solvate                       Inclusion compound with THF X-ray diffractograms

Fig. 3: IR spectra

Raman spectra

FIR spectra

NIR spectra

Fig. 7: DSC thermogram (amorphous form)
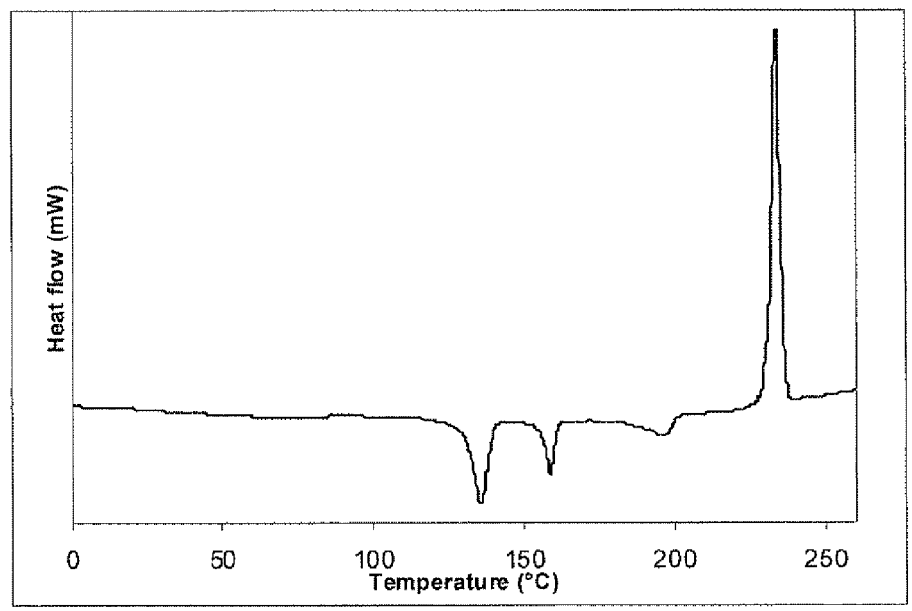
Fig. 8: X-ray diffractogram (amorphous form)
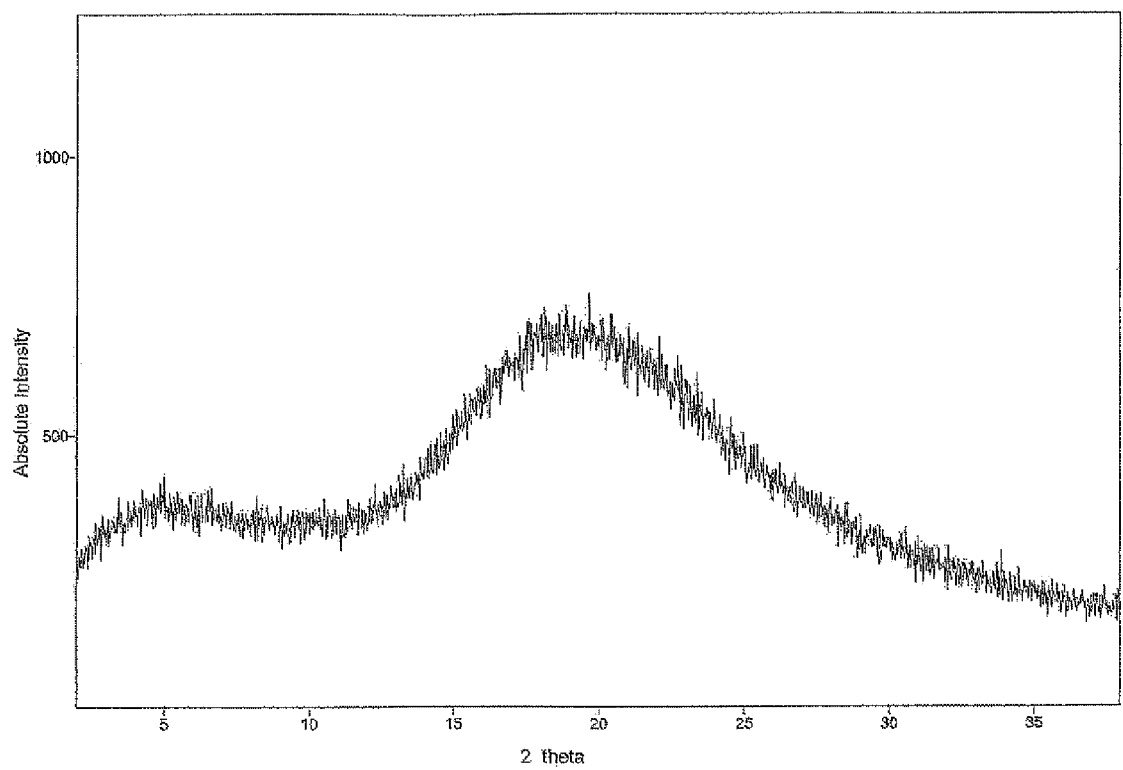

Fig. 9: IR spectrum (amorphous form)
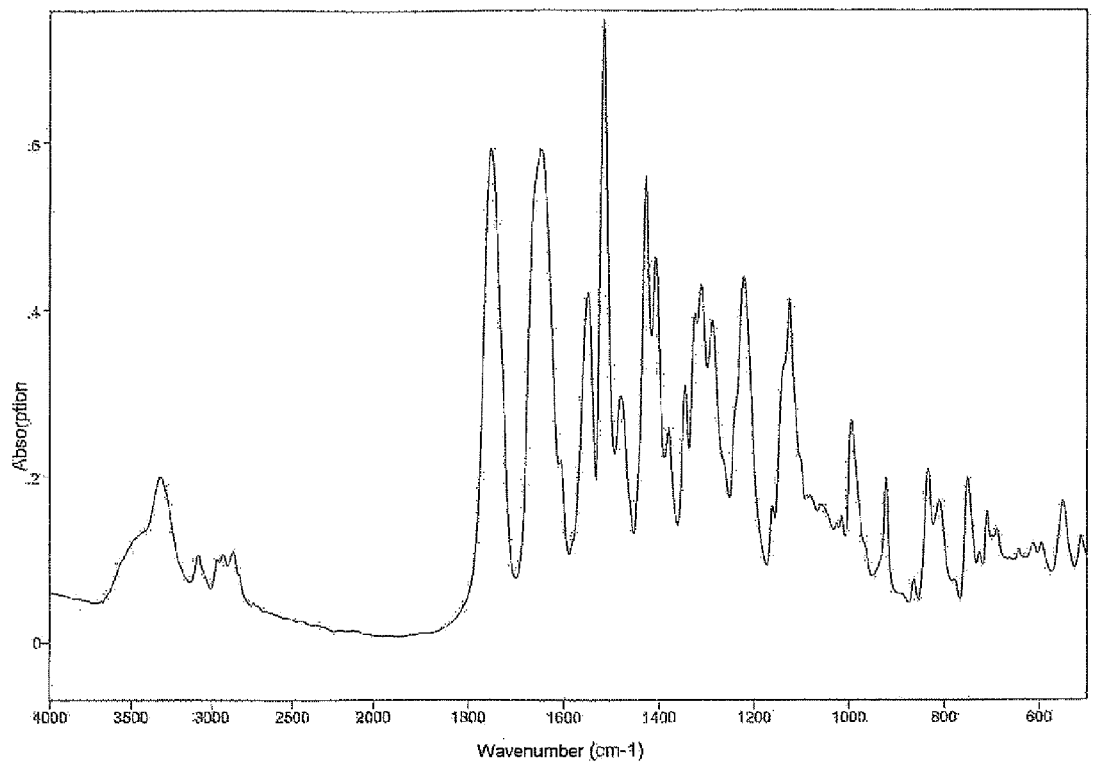
Fig. 10: Raman spectrum (amorphous form)
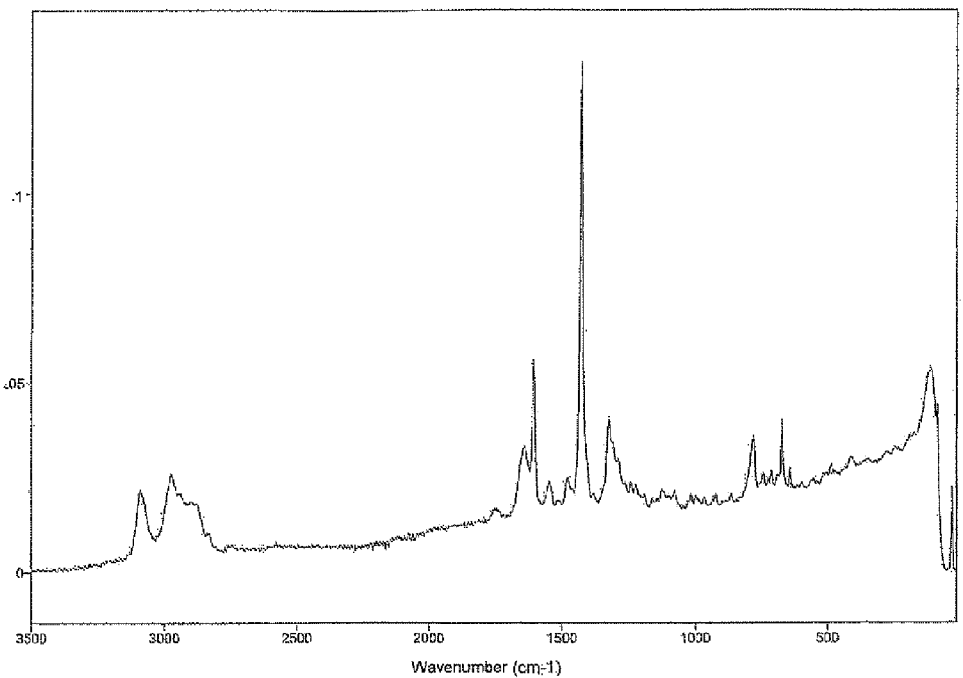

Fig. 11: FIR spectrum (amorphous form)
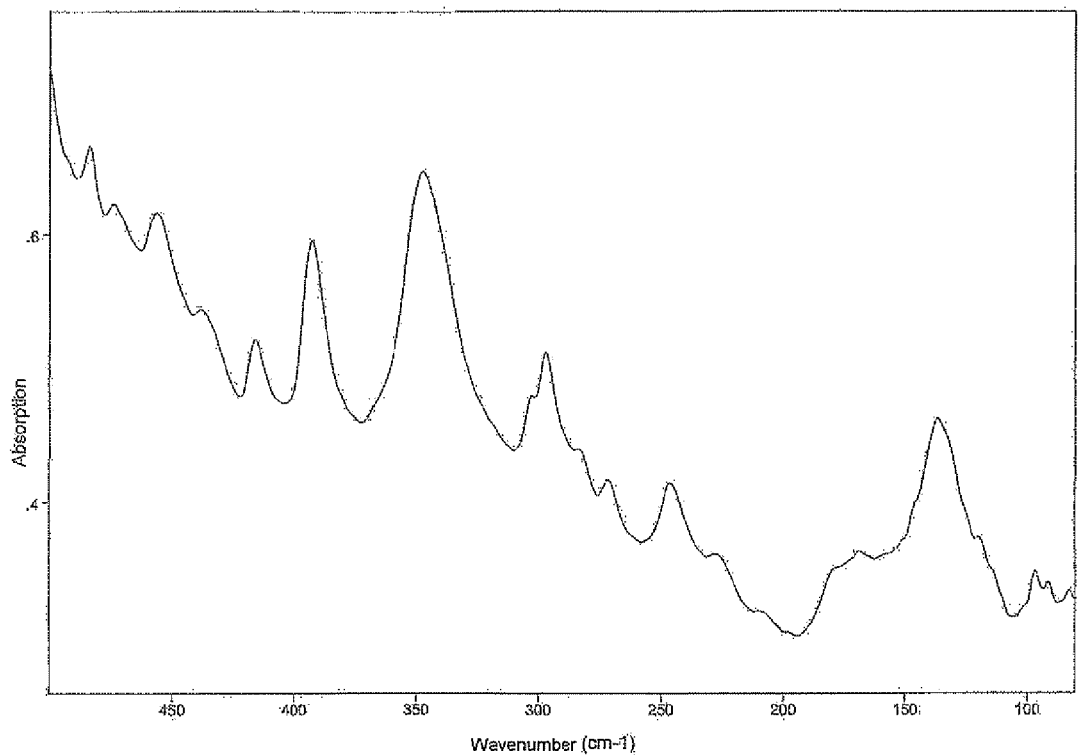
Fig. 12: NIR spectrum (amorphous form)
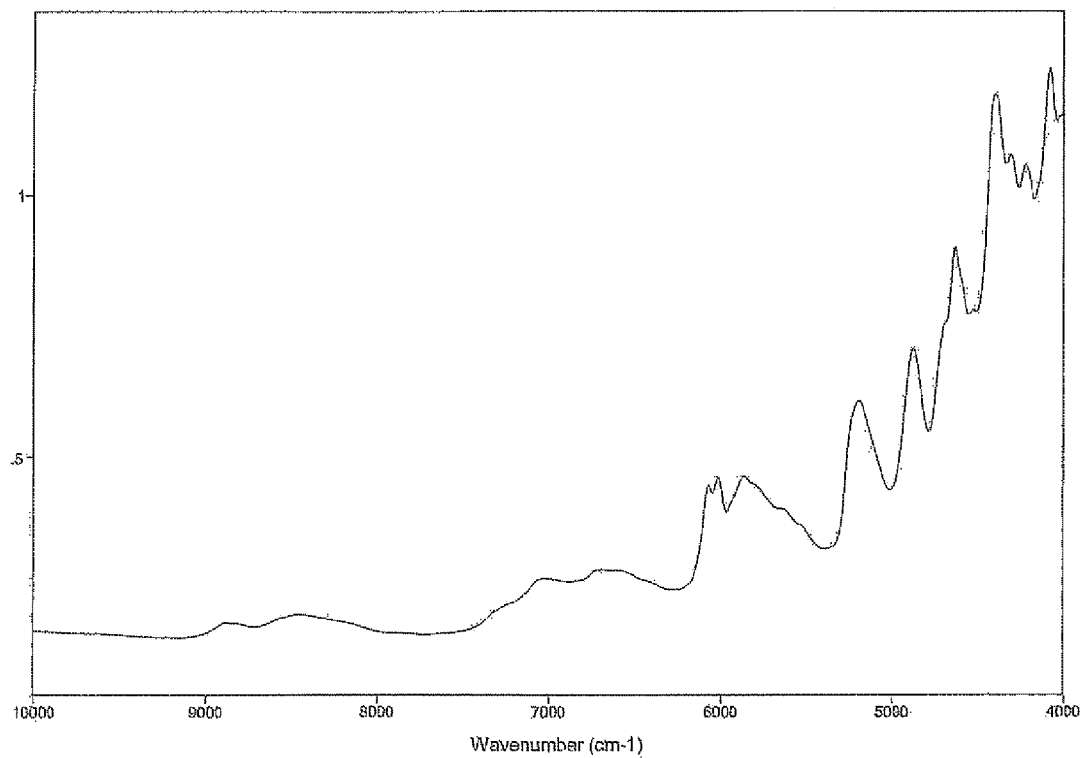

POLYMORPHOUS FORM OF 5-CHLORO-N-({(5S)-2-OXO-3[4-(3-OXO-4-MORPHOLINYL)-PHENYL]-1,3-OXAZOLIDINE-5-YL}-METHYL)-2-THIOPHENE CARBOXAMIDE

RELATED APPLICATIONS

This application is a national stage application (under 35 U.S.C. 371) of PCT/EP2006/009202 filed Sep. 22, 2006, which claims benefit of German application 10 2005 047 564.7 filed Oct. 4, 2005 and German application 10 2005 047 563.9 filed Oct. 4, 2005.

The present invention relates to a novel polymorphic form and the amorphous form of 5-chloro-N-({(5S)-2-oxo-3-[4-(3-oxo-4-morpholinyl)-phenyl]-1,3-oxazolidin-5-yl}-methyl)-2-thiophene-carboxamide, processes for their preparation, medicaments comprising these forms, and their use in the control of diseases.

The compound 5-chloro-N-({(5S)-2-oxo-3-[4-(3-oxo-4-morpholinyl)-phenyl]-1,3-oxazolidin-5-yl}-methyl)-2-thiophenecarboxamide is known from WO 01/47919 and WO 2004/060887 and corresponds to the formula (I):

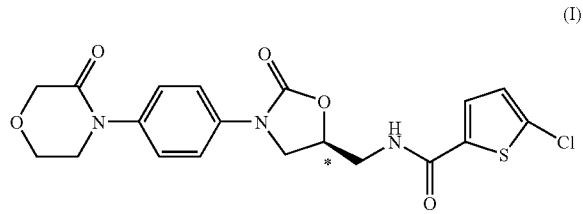

(I)

The compound of the formula (I) is a low molecular weight, orally administrable inhibitor of blood clotting factor Xa, which can be employed for the prophylaxis, secondary prophylaxis and/or treatment of various thromboembolic diseases (for this see WO 01/47919, whose disclosure is included herewith by way of reference), in particular of myocardial infarct, angina pectoris (including unstable angina), reocclusions and restenoses after angioplasty or aortocoronary bypass, cerebral stroke, transitory ischemic attacks, peripheral arterial occlusive diseases, pulmonary embolisms or deep vein thromboses.

The compound of the formula (I) can be prepared as described in WO 01/47919 and WO 2004/060887. The compound of the formula (I) is obtained here in a crystal modification which is designated below as modification I. Modification I has a melting point of 230° C. and a characteristic X-ray diffractogram, IR spectrum, Raman spectrum, FIR spectrum and NIR spectrum (Tab. 1-6, FIG. 1-6). It has now been found that modification I has a solubility lower by the factor 4 in comparison to the modification II.

Surprisingly, two further modifications, a hydrate, an NMP solvate and an inclusion compound with THF of the compound of the formula (I) have been found. The compound of the formula (I) in the modification II melts at approximately 203° C. and has a transition point of approximately 195° C., the compound of the formula (I) in the modification III has a transition point of approximately 127° C. The hydrate contains approximately 4% of water, the NMP solvate contains 18.5% of N-methylpyrrolidone and the inclusion compound with THF approximately 5-7% of tetrahydrofuran.

The present invention relates to the compound of the formula (I) in the modification II. By means of the use according to the invention of the compound of the formula (I) in the modification II, it is ensured that a higher solubility is achieved in comparison to the known modification.

BRIEF DESCRIPTION OF THE DRAWINGS

FIG. 1 shows DSC (solid line) and TGA (dashed line) thermograms for modifications I-III, the hydrate, the NMP solvate, and the inclusion compound with THF.
FIG. 7 shows the DSC thermogram (amorphous form).
FIG. 8 shows the X-ray diffractogram (amorphous form).
FIG. 9 shows the IR spectrum (amorphous form).
FIG. 10 shows the Raman spectrum (amorphous form).
FIG. 11 shows the FIR spectrum (amorphous form).
FIG. 12 shows the NIR spectrum (amorphous form).

Figure 2:
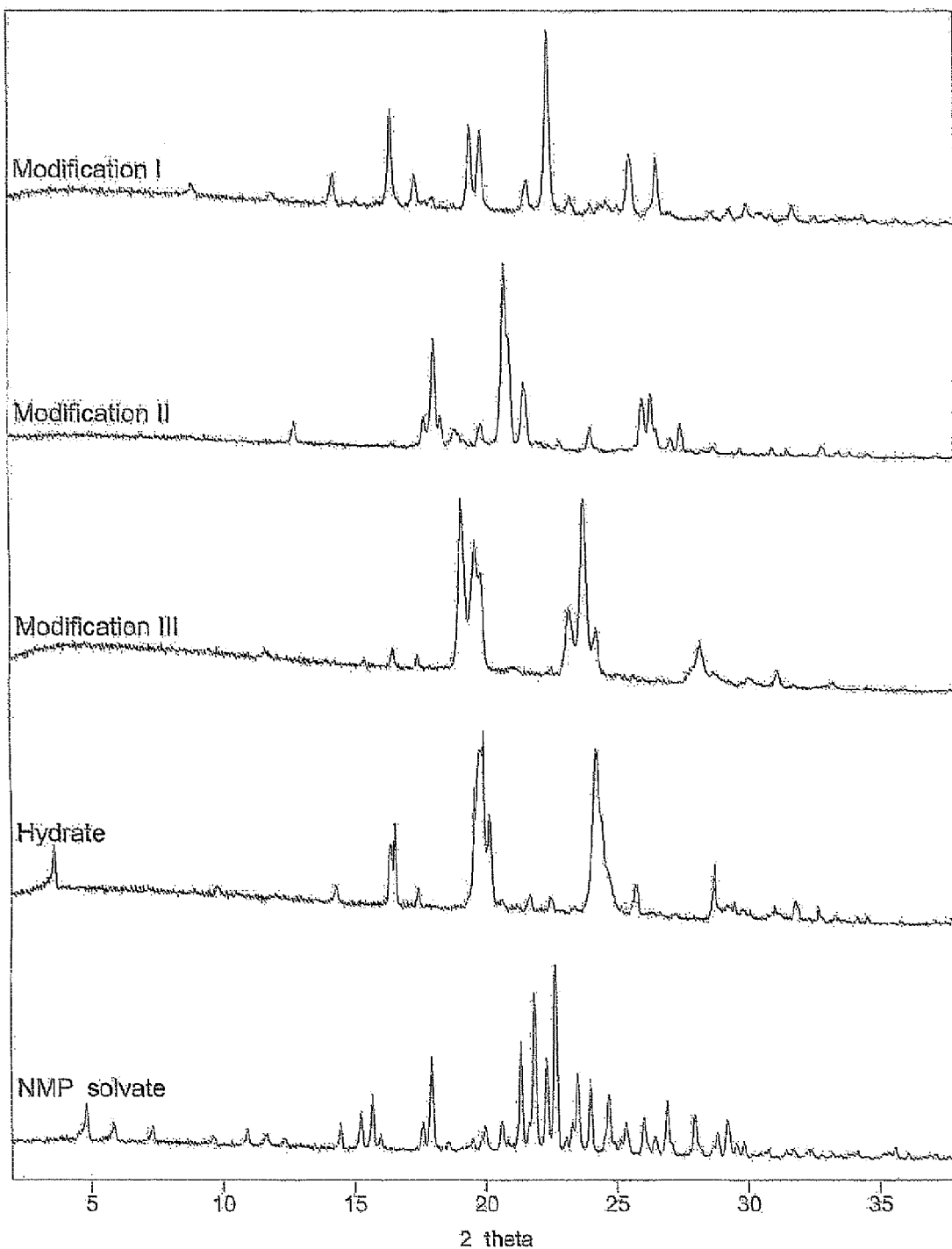
FIG. 2 shows X-ray diffractograms for modifications I-III, the hydrate, and the NMP solvate.
Figure 3:
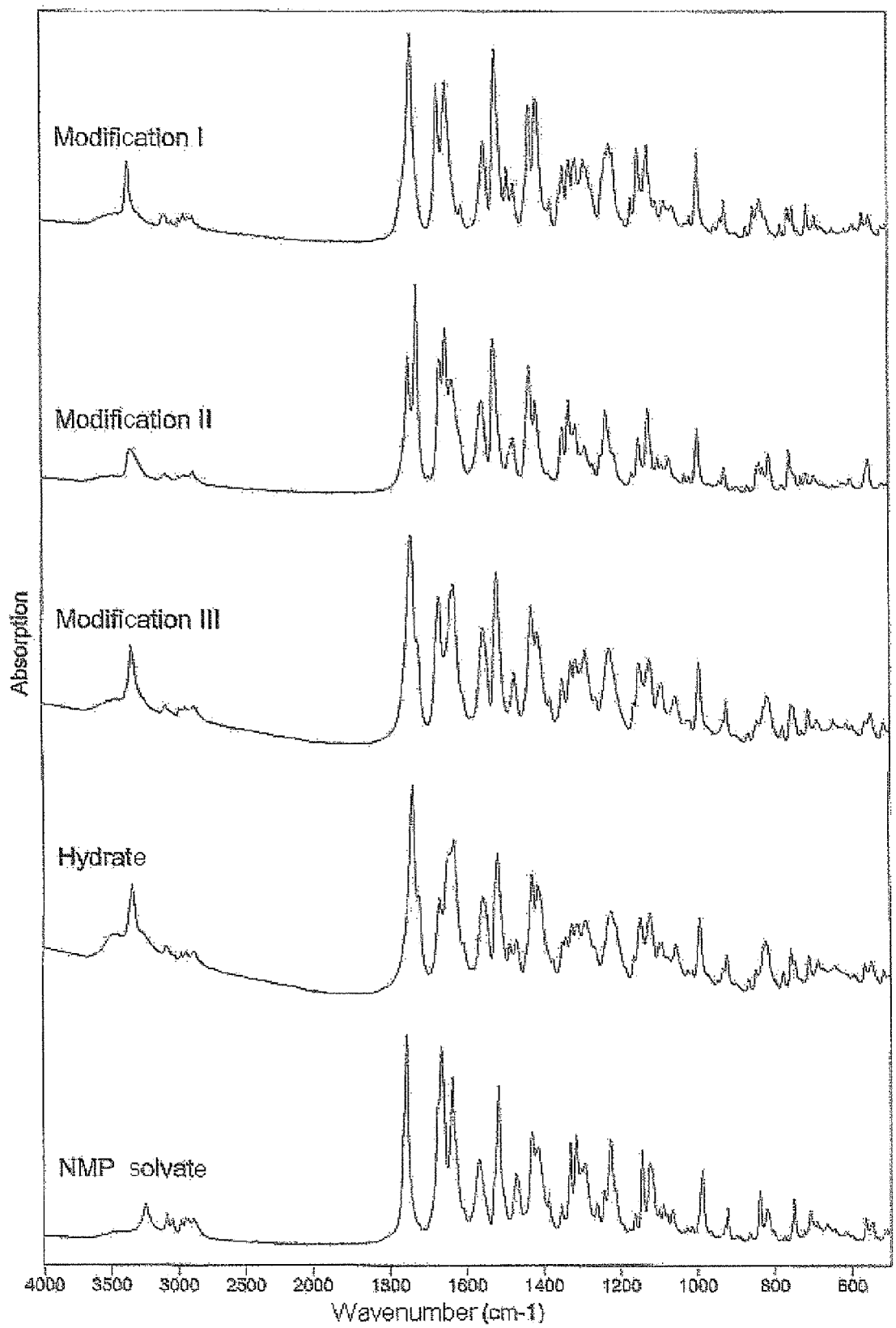
FIG. 3 shows IR spectra for modifications I-III, the hydrate, and the NMP solvate.
Figure 4:
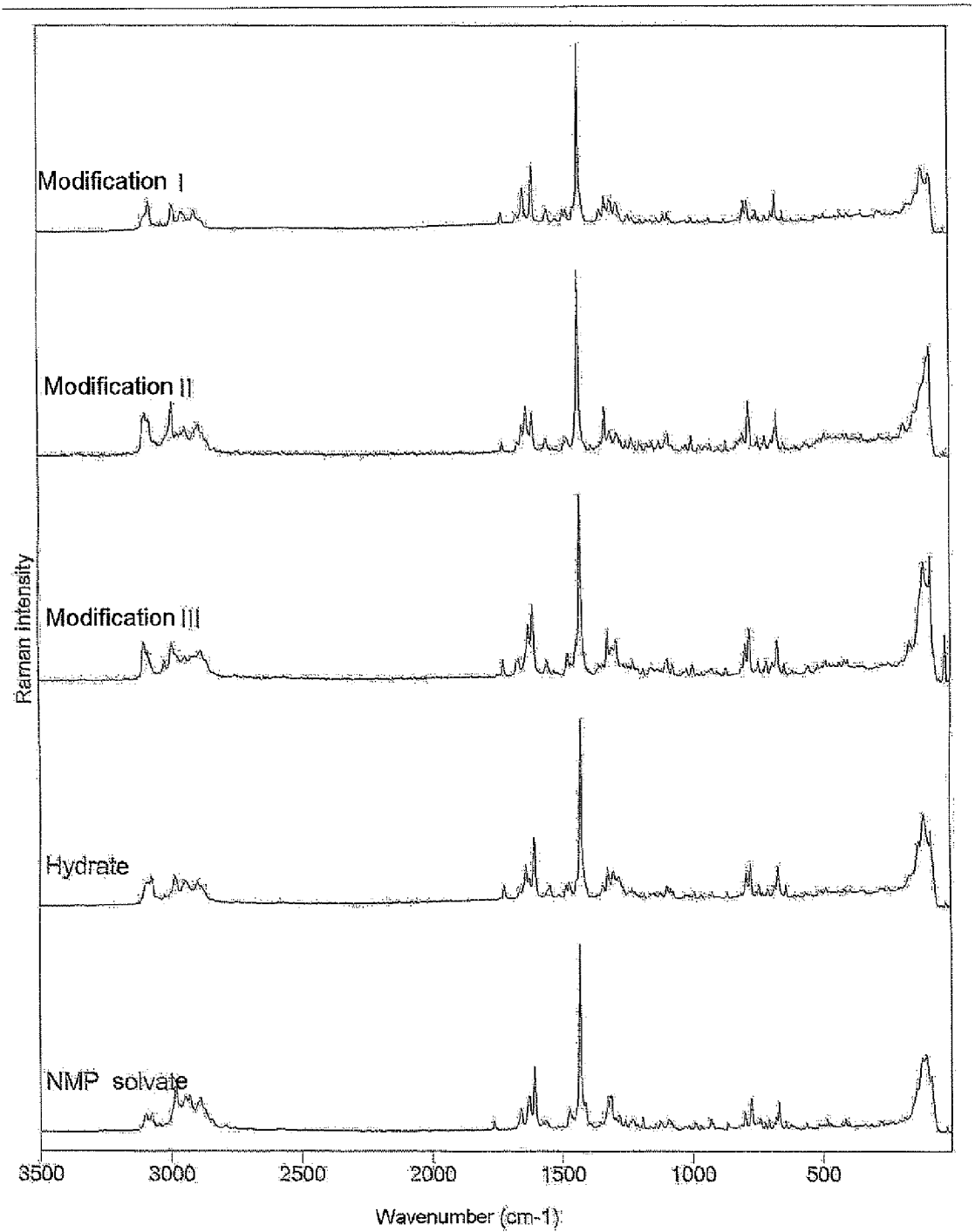
FIG. 4 shows Raman spectra for modifications I-III, the hydrate, and the NMP solvate.
Figure 5:
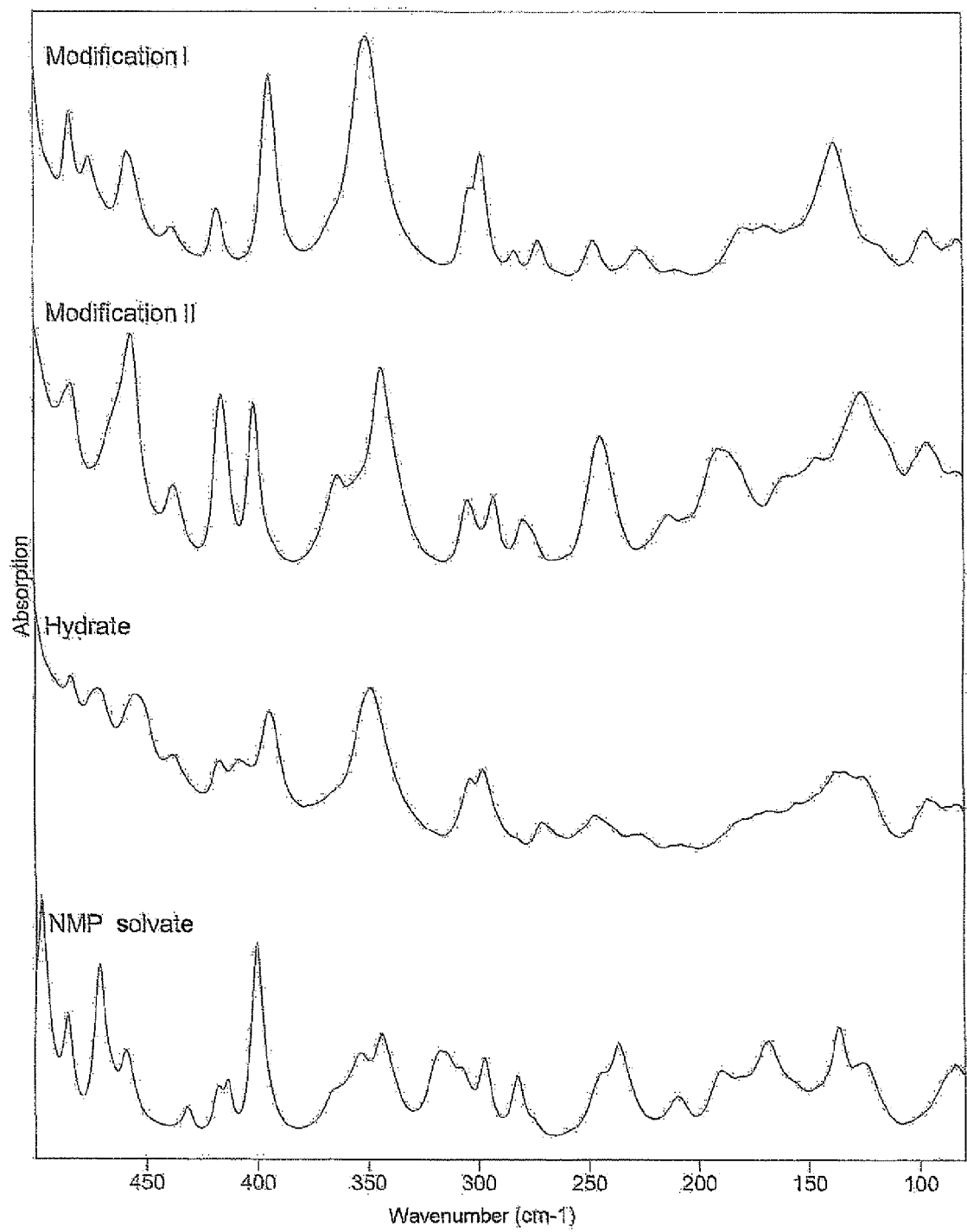
FIG. 5 shows FIR spectra for modifications I-II, the hydrate and the NMP solvate.
Figure 6:
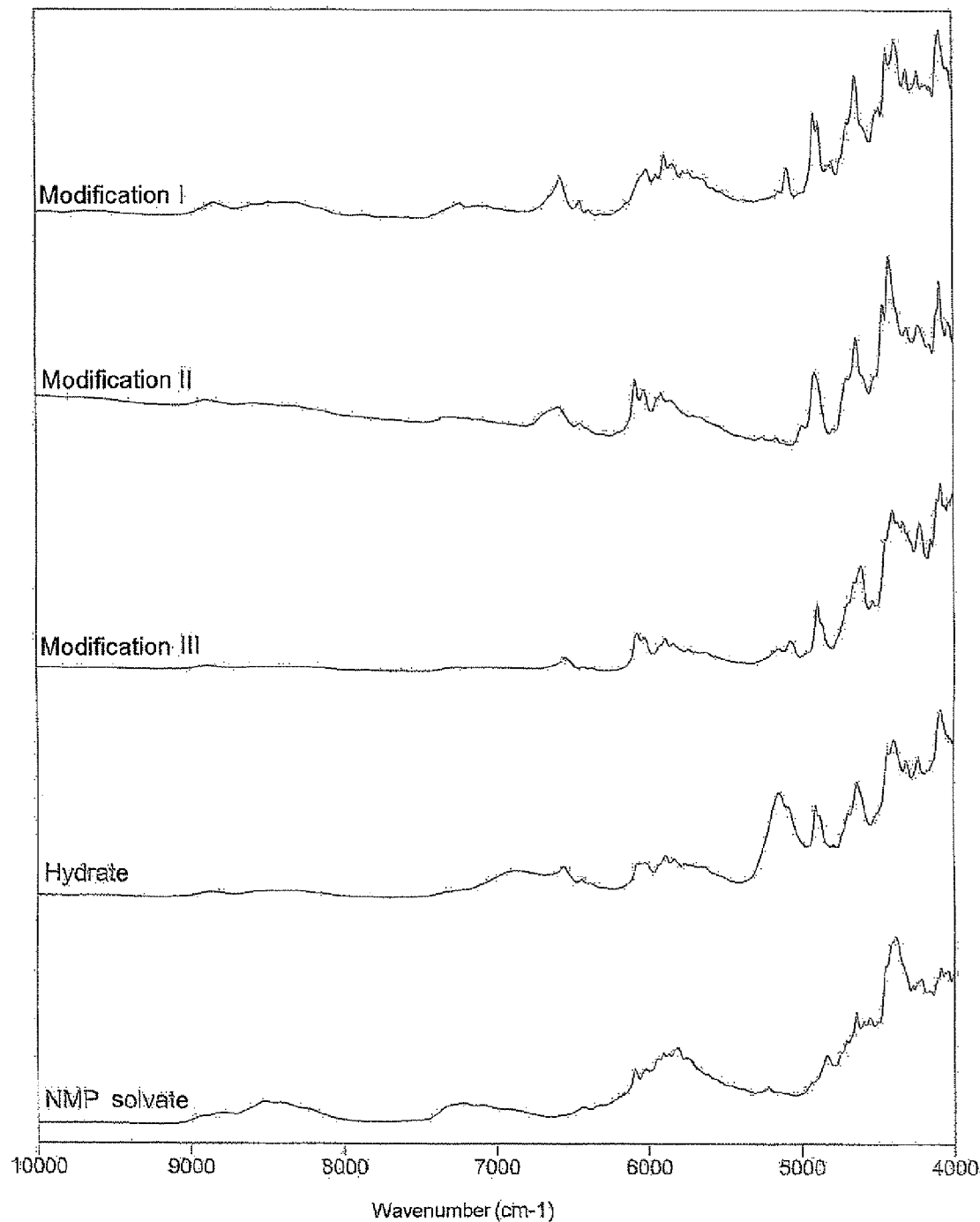
FIG. 6 shows the NIR spectra for modification I-III, the hydrate and the NMP solvate.

Modification II of the compound of the formula (I), in comparison to modification I, modification III, the hydrate form, the NMP solvate and the inclusion compound with THF, has a clearly distinguishable X-ray diffractogram, IR spectrum, NIR spectrum, FIR spectrum and Raman spectrum (FIG. 2-6). The compound of the formula (I) in the modification II melts at 203° C. and converts at approximately 195° C. and is thus clearly distinguishable from modification I (melting point 230° C.) and modification III (transition point approximately 127° C.). In contrast to these solvent-free forms, the hydrate of the compound of the formula (I), the NMP solvate of the compound of the formula (I) and the inclusion compound with THF of the compound of the formula (I) show mass losses in thermogravimetric analysis (TGA) of 4%, 18.5% and 5-7% respectively (FIG. 1).

It is generally known that crystalline polymorphic forms have a poorer water solubility than the amorphous form. This leads to a lower bioavailability in comparison to the amorphous form.

The present invention furthermore relates to the compound of the formula (I) in amorphous form. By means of the use according to the invention of the compound of the formula (I) in the amorphous form, it is ensured that maximum bioavailability is achieved.

The amorphous form of the compound of the formula (I) has a characteristic X-ray diffractogram, NIR spectrum, FIR spectrum and Raman spectrum (FIG. 8-12). The compound of the formula (I) in the amorphous form has a glass transition temperature of approximately 83° C. (DSC, FIG. 7).

The compound of the formula (I) according to the invention in the modification II or in the amorphous form is employed in high purity in pharmaceutical formulations. For reasons of stability, a pharmaceutical formulation mainly contains the compound of the formula (I) in the modification II or in the amorphous form and no relatively large proportions of another form such as, for example, of another modification or of a solvate of the compound of the formula (I). Preferably, the medicament contains more than 90 percent by weight, particularly preferably more than 95 percent by weight of the compound of the formula (I) in the modification II or in the amorphous form based on the total amount of the compound of the formula (I) contained.

The present invention further relates to the use of the compound of the formula (I) in the modification II or in the amorphous form for the treatment and/or prophylaxis of diseases, preferably of thromboembolic diseases and/or thromboembolic complications.

The "thromboembolic diseases" within the meaning of the present invention in particular include diseases such as myocardial infarct with ST segment elevation (STEMI) and without ST segment elevation (non-STEMI), stable angina pectoris, unstable angina pectoris, reocclusions and restenoses after coronary interventions such as angioplasty or aortocoronary bypass, peripheral arterial occlusive diseases, pulmonary embolisms, deep vein thromboses and renal vein thromboses, transitory ischemic attacks, and thrombotic and thromboembolic cerebral stroke.

The compound according to the invention is therefore also suitable for the prevention and treatment of cardiogenic thromboembolisms, such as, for example, cerebral ischemias, stroke and systemic thromboembolisms and ischemias in patients with acute, intermittent or persistent cardiac arrhythmias, such as, for example, atrial fibrillation, and those who are subject to cardioversion, furthermore in the case of patients with heart valve diseases or with artificial heart valves. Moreover, the compound according to the invention is suitable for the treatment of disseminated intravasal clotting (DIC).

Thromboembolic complications furthermore occur in microangiopathic hemolytic anemias, extracorporeal blood circulations, such as hemodialysis, and heart valve prostheses.

Moreover, the compound according to the invention is also suitable for the prophylaxis and/or treatment of atherosclerotic vascular diseases and inflammatory diseases such as rheumatic diseases of the locomotor system, moreover also for the prophylaxis and/or treatment of Alzheimer's disease. Moreover, the compound according to the invention can be employed for the inhibition of tumor growth and of metastasis formation, in microangiopathies, age-related macular degeneration, diabetic retinopathy, diabetic nephropathy and other microvascular diseases, and for the prevention and treatment of thromboembolic complications, such as, for example, venous thromboembolisms, in tumor patients, in particular those who are subjected to relatively large surgical interventions or chemo- or radiotherapy.

The compound according to the invention can moreover be employed for the prevention of coagulation ex vivo, e.g. for the preservation of blood and plasma products, for the cleaning/pretreatment of catheters and other medical aids and equipment, for the coating of artificial surfaces of medical aids and equipment employed in vivo or ex vivo or in biological samples which contain factor Xa.

The present invention further relates to the use of the compound according to the invention for the treatment and/or prophylaxis of diseases, in particular of the aforementioned diseases.

The present invention furthermore relates to the use of the compound according to the invention for the production of a medicament for the treatment and/or prophylaxis of diseases, in particular of the aforementioned diseases.

The present invention furthermore relates to a process for the treatment and/or prophylaxis of diseases, in particular of the aforementioned diseases, using an amount of the compound according to the invention having anticoagulatory activity.

The present invention furthermore relates to a process for the prevention of blood coagulation in vitro, in particular in blood preserves or biological samples which contain factor Xa, which is characterized in that an amount of the compound according to the invention having anticoagulatory activity is added.

The present invention furthermore relates to medicaments comprising the compound according to the invention and one or more other active substances, in particular for the treatment and/or prophylaxis of the aforementioned diseases. Suitable combination active substances which may be mentioned by way of example and preferably are:

lipid-lowering agents, in particular HMG-CoA-(3-hydroxy-3-methylglutaryl-coenzyme A)-reductase inhibitors;

coronary therapeutics/vasodilators, in particular ACE (angiotensin converting enzyme) inhibitors; AII (angiotensin II) receptor antagonists; β-adrenoceptor antagonists; alpha-1-adrenoceptor antagonists; diuretics; calcium channel blockers; substances which bring about an increase in cyclic guanosine monophosphate (cOMP), such as, for example, stimulators of soluble guanylate cyclase;

plasminogen activators (thrombolytics/fibrinolytics) and thrombolysis/fibrinolysis-increasing compounds such as inhibitors of the plasminogen activator inhibitor (PAI inhibitors) or inhibitors of the thrombin-activated fibrinolysis inhibitor (TAFI inhibitors);

substances having anticoagulatory activity (anticoagulants);

substances inhibiting platelet aggregation (platelet aggregation inhibitors, thrombocyte aggregation inhibitors);

and fibrinogen receptor antagonists (glycoprotein IIb/IIIa antagonists).

The present invention further relates to medicaments which contain the compound according to the invention, customarily together with one or more inert, nontoxic, pharmaceutically suitable excipients, and their use for the aforementioned purposes.

The compound according to the invention can act systemically and/or locally. For this purpose, they can be administered in a suitable manner, such as, for example, orally, parenterally, pulmonarily, nasally, sublingually, lingually, buccally, rectally, dermally, transdermally, conjunctivally, otically or as an implant or stent.

For these administration routes, the compound according to the invention can be administered in suitable administration forms.

For oral administration, administration forms functioning according to the prior art, releasing the compound according to the invention rapidly and/or in modified form, which contain the compound of the formula (I) in the modification II or in the amorphous form, such as, for example, tablets (non-coated or coated tablets, for example with enteric coatings or coatings which dissolve with a delay or are insoluble, which control the release of the compound according to the invention), tablets disintegrating rapidly in the oral cavity or films/wafers, films/lyophilizates, capsules (for example hard or soft gelatin capsules), coated tablets, granules, pellets, powders, suspensions or aerosols are suitable.

Parenteral administration can take place with circumvention of an absorption step (e.g. intravenously, intraarterially, intracardially, intraspinally or intralumbarly) or with intervention of an absorption (e.g. intramuscularly, subcutaneously, intracutaneously, percutaneously or intraperitoneally). For parenteral administration, suitable administration forms are, inter alia, injection and infusion preparations in the form of suspensions, lyophilizates or sterile powders.

For the other administration routes, for example, inhalation pharmaceutical forms (inter alia powder inhalers, nebulizers), tablets to be administered lingually, sublingually or buccally, films/wafers or capsules, suppositories, ear or eye preparations, vaginal capsules, aqueous suspensions (lotions, shake mixtures), lipophilic suspensions, ointments, creams, transdermal therapeutic systems (e.g. patches), milk, pastes, foams, dusting powders, implants or stents are suitable.

Oral or parenteral administration is preferred, in particular oral administration.

The compound according to the invention can be converted to the administration forms mentioned. This can take place in a manner known per se by mixing with inert, nontoxic, pharmaceutically suitable excipients. These excipients include, inter alia, vehicles (for example microcrystalline cellulose, lactose, mannitol), solvents (e.g. liquid polyethylene glycols), emulsifiers and dispersants or wetting agents (for example sodium dodecylsulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and taste and/or odor corrigents.

In general, it has proven advantageous in the case of parenteral administration to administer amounts of approximately 0.001 to 1 mg/kg, preferably approximately 0.01 to 0.5 mg/kg of body weight to achieve effective results. In the case of oral administration, the dose is approximately 0.01 to 100 mg/kg, preferably approximately 0.01 to 20 mg/kg and very particularly preferably 0.1 to 10 mg/kg of body weight.

In spite of this, it may optionally be necessary to depart from the amounts mentioned, namely depending on body weight, route of administration, individual behavior toward the medicament, type of preparation and time or interval at which administration takes place. Thus in some cases it may be adequate to manage with less than the aforementioned minimum amount, whereas in other cases the upper limit mentioned must be exceeded. In the case of the administration of relatively large amounts, it may be advisable to divide these into a number of individual doses over the course of the day.

The invention further relates to a process for the preparation of the compound of the formula (I) in the modification II, by dissolving the compound of the formula (I) in the modification I in an inert solvent and precipitating the active substance by addition of a precipitating agent at a temperature between 0° C. and 80° C., preferably from 20 to 25° C. The precipitate is isolated and dried. The compound of the formula (I) is thus obtained in the modification II.

The invention likewise relates to a process for the preparation of the compound of the formula (I) in the modification II, by dissolving the compound of the formula (I) in the modification I in an inert solvent and storing it, preferably at elevated temperature, in particular at a temperature of 30° C. up to the reflux temperature of the solvent, until the complete evaporation of the solvent and crystallization of the active substance. The compound of the formula (I) is thus obtained in the modification II.

The invention likewise relates to a process for the preparation of the compound of the formula (I) in the modification II, by suspending the compound of the formula (I) in the amorphous form in an anhydrous inert solvent and stirring or shaking it until achieving the desired degree of conversion, in particular until quantitative conversion, to the modification II. The crystallizate obtained is isolated and dried. The compound of the formula (I) is thus obtained in the modification II.

Suitable inert solvents are lower alcohols such as, for example, methanol, ethanol, n-propanol, iso-propanol, n-butanol, sec-butanol, isobutanol, 1-pentanol, or ketones such as acetone, or alkanes such as n-pentane, cyclopentane, n-hexane, cyclohexane, or tetrahydrofuran, or acetonitrile, or toluene, or ethyl acetate, or 1,4-dioxane, or mixtures of the solvents mentioned, or mixtures of the solvents mentioned with water. Acetone, tetrahydrofuran, 1-pentanol or mixtures of the solvents mentioned are preferred. Suitable precipitating agents are inert, anhydrous solvents, in which the active substance is poorly soluble, such as, for example, n-heptane, cyclohexane or toluene. n-Heptane is preferred.

Preferably, the compound of the formula (I) is prepared in the modification II, by dissolving the compound of the formula (I) in the modification I in acetone or tetrahydrofuran and precipitating the active substance by addition of n-heptane at a temperature between 0 and 80° C., preferably at a temperature from 20 to 25° C. The precipitate is isolated and dried. The compound of the formula (I) is thus obtained in the modification II.

Likewise preferably, the compound of the formula (I) is prepared in the modification II, by dissolving the compound of the formula (I) in the modification I in 1,4-dioxane and storing at elevated temperature, in particular at a temperature from. 30° C. up to the reflux temperature of the solvent, for example 50° C., until the complete evaporation of the solvent and crystallization of the active substance. The compound of the formula (I) is thus obtained in the modification II.

Likewise preferably, the compound of the formula (I) is prepared in the modification II, by suspending the compound of the formula (I) in the amorphous form in an inert anhydrous solvent and stirring or shaking at a temperature of 20 to 25° C. until achieving the desired degree of conversion to the modification II. The crystallizate obtained is isolated and dried. The compound of the formula (I) is thus obtained in the modification II.

The invention further relates to a process for the preparation of the compound of the formula (I) in the amorphous form, in which the compound of the formula (I) in a crystalline form is fused and subsequently rapidly cooled. The compound of the formula (I) is thus obtained in the amorphous form.

Preferably, the compound of the formula (I) is prepared in the amorphous form, by fusing the compound of the formula (I) in a crystalline form at a temperature of at least 230° C., in particular at a temperature of 240 to 250° C., and subsequently rapidly cooling it. The compound of the formula (I) is thus obtained in the amorphous form.

Of the crystalline forms modification I, II and III, preferably modification I or II, are employed here, in particular modification I.

By means of rapid cooling, the temperature of the compound (I) is preferably brought to or close to room temperature, for example to a temperature of approximately 15 to 30° C., in particular of approximately 20 to 25° C. The rapid cooling is preferably carried out in the course of a few seconds, for example in the course of approximately 5 seconds. Shock cooling is preferably employed for rapid cooling.

The compound of the formula (I) in the modification III can be prepared by dissolving the compound of the formula (I) in the modification I in an inert solvent, for example acetone. The solution is treated with water and allowed to stand at room temperature until the solvent has completely evaporated. The compound of the formula (I) is thus obtained in the modification III.

The hydrate of the compound of the formula (I) can be prepared by dissolving the compound of the formula (I) in the modification I in ethanol:water (1:1). The solution is a stored at a temperature of approximately −20° C. until the solvent has evaporated. The hydrate of the compound of the formula (I) is thus obtained.

The NMP solvate of the compound of the formula (I) can be prepared by suspending the compound of the formula (I) in the modification I in 1-methyl-2-pyrrolidone and stirring at room temperature. After 2 days, the suspension is filtered and the product is dried. The NMP solvate of the compound of the formula (I) with an NMP content of 18.5 percent by weight is thus obtained.

The inclusion compound with THF of the compound of the formula (I) can be prepared by dissolving the compound of the formula (I) in the modification I in tetrahydrofuran. The solution is stored at room temperature until the solvent has evaporated. The inclusion compound with THF of the compound of the formula (I) is thus obtained.

The percentages in the following tests and examples, if not stated otherwise, are percentages by weight; parts are parts by weight. Solvent ratios, dilution ratios and concentration data of liquid/liquid solutions in each case relate to the volume.

WORKING EXAMPLES

The thermograms were obtained using a DSC 7 or Pyris-1 differential scanning calorimeter and TGA 7 thermogravimetric analyzer from Perkin-Elmer. The X-ray diffractograms were recorded in a Stoe transmission diffractometer. The IR, FIR, NIR and Raman spectra were recorded using IFS 66v Fourier IR (IR, FIR), IFS 28/N (NIR) and RFS 100 (Raman) spectrometers from Bruker.

Example 1

5-Chloro-N-({(5S)-2-oxo-3-[4-(3-oxo-4-morpholinyl)-phenyl]-1,3-oxazolidin-5-yl}-methyl)-2-thiophenecarboxamide in the Modification I The preparation of the modification I of the title compound is described in WO 01/47919 and WO 2004/060887.

Example 2

Preparation of 5-chloro-N-({(5S)-2-oxo-3-[4-(3-oxo-4-morpholinyl)-phenyl]-1,3-oxazolidin-5-yl}-methyl)-2-thiophenecarboxamide in the Modification II Example 2.1

208 g of chlorothiophenecarboxylic acid were suspended in 1100 ml of toluene and heated to 75 to 80° C. 112 ml of thionyl chloride were added dropwise at this temperature in the course of 2 h. The resulting reaction solution was stirred for a further 2 h until the end of evolution of gas. In the course of this, the internal temperature was increased to 100-110° C. in 5° steps. The mixture was cooled and the solution of the acid chloride was concentrated on a rotary evaporator.

350 g of oxamine hydrochloride were suspended in 2450 ml of NMP, treated with 385 ml of triethylamine and stirred for 15 min. The mixture was cooled to 10° C., treated with the solution of the acid chloride and 70 ml of toluene and stirred. 350 ml of tap water were added to the suspension and it was heated to 82° C. After filtration, the active substance was precipitated using 3.5 l of water and the mixture was subsequently stirred for 2 h. Drying at 70° C. in vacuo.

Example 2.2

About 200 mg of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were dissolved hot in about 80 ml of tetrahydrofuran. The solution was filtered and divided in half. One half was treated at room temperature with n-heptane until the active substance precipitated. The residue was filtered off and dried at room temperature. It was investigated by X-ray diffractometry and corresponded to the title compound in the modification II.

Example 2.3

About 200 mg of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were dissolved hot in about 40 ml of 1-pentanol. The solution was filtered and divided in half. One half was treated with n-heptane until the active substance precipitated. The residue was filtered off and dried at room temperature. It was investigated by X-ray diffractometry and corresponded to the title compound in the modification II.

Example 2.4

About 200 mg of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were dissolved hot in about 40 ml of 1,4-dioxane. The solution was filtered and divided in half. One half was stored at 50° C. in a drying oven until the solvent had evaporated. The residue was investigated by X-ray diffractometry and corresponded to the title compound in the modification II.

Example 2.5

About 50 mg of 5-chloro-N-({(5S)-2-oxo-3-[4-(3-oxo-4-morpholinyl)-phenyl]-1,3-oxazolidin-5-yl}-methyl)-2-thiophenecarboxamide in the amorphous form, prepared by fusing on a Kofler heating bench at about 240° C. and subsequent shock cooling to room temperature, were suspended in about 2 ml of ethanol and stirred at 25° C. for 0.5 h. The crystallizate was isolated and dried. The residue was investigated by X-ray diffractometry and corresponded to the title compound in the modification II.

Example 2.6

About 100 mg of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were dissolved hot in about 50 ml of acetone. The solution was filtered and treated with n-heptane in an ice bath until the active substance precipitated. The residue was filtered off and dried at room temperature. It was investigated by X-ray diffractometry and corresponded to the title compound in the modification II.

Example 3

Preparation of 5-chloro-N-({(5S)-2-oxo-3-[4-(3-oxo-4-morpholinyl)-phenyl]-1,3-oxazolidin-5-yl}-methyl)-2-thiophenecarboxamide in the Modification III About 120 mg of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were dissolved hot in about 50 ml of acetone. The solution was filtered, treated with about 50 ml of water and allowed to stand at room temperature until the solvent had evaporated. The residue was investigated thermoanalytically and corresponded to the title compound in the modification III.

Example 4

Preparation of the Hydrate of 5-chloro-N-({(5S)-2-oxo-3-[4-(3-oxo-4-morpholinyl)-phenyl]-1,3-oxazolidin-5-yl}-methyl)-2-thiophenecarboxamide About 400 mg of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were dissolved hot in about 60 ml of ethanol:water (1:1) and filtered. A part of the solution was stored in a freezer at a temperature of approximately −20° C. until the solvent had evaporated. The residue corresponded to the hydrate of the title compound.

Example 5

Preparation of the NMP Solvate of 5-chloro-N-({(5S)-2-oxo-3-[4-(3-oxo-4-morpholinyl)-phenyl]-1,3-oxazolidin-5-yl}-methyl)-2-thiophenecarboxamide About 3.5 g of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were suspended in 10 ml of 1-methyl-2-pyrrolidone and stirred at room temperature. After a few hours, about 20 ml of NMP were additionally added. After two days, the suspension was filtered off with suction and the residue was dried at room temperature. The residue was investigated thermoanalytically and corresponded to the NMP solvate of the title compound having an NMP content of 18.5 percent by weight.

Example 6

Preparation of the Inclusion Compound with THF of 5-chloro-N-({(5S)-2-oxo-3-[4-(3-oxo-4-morpholinyl)-phenyl]-1,3-oxazolidin-5-yl}-methyl)-2-thiophenecarboxamide About 400 mg of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were dissolved hot in about 50 ml of tetrahydrofuran and filtered. A part of the solution was stored at room temperature until the solvent had evaporated. The residue was investigated thermoanalytically and corresponded to the inclusion compound with THF of the title compound.

TABLE 1

Differential scanning calorimetry and thermogravimetry

| | Modification I | Modification II | Modification III | Hydrate | NMP solvate | ESV toluene |
|---|---|---|---|---|---|---|
| Melting point [° C.] | 230 | 203 | — | — | — | — |
| Transition point [° C.] | — | ca. 192 | ca. 127 | — | — | — |
| Mass loss [% by wt.] | 0.1 | 0.1 | <0.5 | ca. 4 | 18.5 | 5-7 |

TABLE 2

X-ray diffractometry Reflections

| Modification I [2 theta] | Modification II [2 theta] | Modification III [2 theta] | Hydrate [2 theta] | NMP solvate [2 theta] | ESV with THF [2 theta] |
|---|---|---|---|---|---|
| 8.9 | 12.8 | 11.7 | 3.6 | 4.8 | 9.0 |
| 12.0 | 17.7 | 16.5 | 14.3 | 5.8 | 12.0 |
| 14.3 | 18.1 | 17.5 | 16.4 | 7.3 | 14.3 |
| 16.5 | 18.4 | 19.1 | 16.6 | 10.9 | 14.7 |
| 17.4 | 19.0 | 19.6 | 17.5 | 14.5 | 16.5 |
| 18.1 | 19.9 | 19.8 | 19.3 | 15.2 | 16.8 |
| 19.5 | 20.8 | 23.1 | 19.6 | 15.7 | 17.5 |
| 19.9 | 21.6 | 23.2 | 19.9 | 16.0 | 19.6 |
| 21.7 | 22.1 | 23.8 | 20.2 | 17.6 | 19.9 |
| 22.5 | 22.9 | 24.3 | 21.7 | 17.9 | 21.7 |
| 23.4 | 24.1 | 28.1 | 22.5 | 20.0 | 22.5 |
| 24.1 | 26.1 | 28.2 | 24.2 | 20.6 | 23.4 |
| 24.5 | 26.4 | 31.2 | 25.6 | 21.3 | 24.5 |
| 24.7 | 26.6 | | 25.8 | 21.8 | 24.7 |
| 25.6 | 27.2 | | 28.8 | 22.3 | 25.2 |
| 26.4 | 27.5 | | 29.5 | 22.7 | 25.6 |
| 26.7 | 28.8 | | 31.8 | 23.1 | 26.4 |
| 30.0 | 29.8 | | 32.7 | 23.3 | 26.7 |
| 30.1 | 31.0 | | | 23.5 | 28.7 |
| 31.8 | 31.6 | | | 24.0 | 30.1 |
| | 32.9 | | | 24.7 | 31.0 |
| | | | | 24.9 | 31.8 |
| | | | | 25.2 | |
| | | | | 26.0 | |
| | | | | 26.5 | |
| | | | | 26.9 | |
| | | | | 28.0 | |
| | | | | 28.8 | |
| | | | | 29.2 | |
| | | | | 29.5 | |
| | | | | 29.8 | |

TABLE 3

IR spectroscopy Peak maxima

| Modification I [cm$^{-1}$] | Modification II [cm$^{-1}$] | Modification III [cm$^{-1}$] | Hydrate [cm$^{-1}$] | NMP solvate [cm$^{-1}$] |
|---|---|---|---|---|
| 564 | 552 | 515 | 708 | 497 |
| 686 | 598 | 546 | 755 | 547 |
| 708 | 692 | 596 | 776 | 562 |
| 746 | 713 | 611 | 820 | 708 |
| 757 | 725 | 644 | 920 | 749 |
| 830 | 756 | 688 | 992 | 819 |
| 846 | 809 | 709 | 1054 | 838 |
| 920 | 825 | 748 | 1089 | 921 |
| 991 | 833 | 755 | 1120 | 987 |
| 1011 | 924 | 776 | 1146 | 1065 |
| 1056 | 994 | 812 | 1221 | 1088 |
| 1077 | 1067 | 816 | 1289 | 1123 |
| 1120 | 1085 | 842 | 1312 | 1143 |
| 1146 | 1097 | 864 | 1324 | 1162 |
| 1163 | 1121 | 921 | 1340 | 1225 |
| 1219 | 1146 | 992 | 1349 | 1242 |
| 1286 | 1232 | 1016 | 1413 | 1260 |
| 1307 | 1285 | 1054 | 1429 | 1292 |
| 1323 | 1310 | 1089 | 1469 | 1302 |
| 1341 | 1328 | 1121 | 1485 | 1315 |
| 1374 | 1345 | 1148 | 1518 | 1330 |
| 1411 | 1415 | 1161 | 1555 | 1354 |
| 1429 | 1431 | 1224 | 1630 | 1387 |
| 1470 | 1473 | 1261 | 1668 | 1414 |
| 1486 | 1523 | 1288 | 1738 | 1421 |
| 1517 | 1554 | 1313 | 2873 | 1430 |
| 1546 | 1631 | 1325 | 3341 | 1471 |
| 1605 | 1648 | 1348 | | 1517 |
| 1646 | 1663 | 1380 | | 1566 |

TABLE 3-continued

IR spectroscopy
Peak maxima

| Modification I [cm$^{-1}$] | Modification II [cm$^{-1}$] | Modification III [cm$^{-1}$] | Hydrate [cm$^{-1}$] | NMP solvate [cm$^{-1}$] |
|---|---|---|---|---|
| 1669 | 1723 | 1412 | | 1636 |
| 1737 | 1745 | 1429 | | 1665 |
| 2867 | 3341 | 1473 | | 1755 |
| 2895 | | 1518 | | 2887 |
| 2936 | | 1553 | | 2928 |
| 2976 | | 1629 | | 2948 |
| 3354 | | 1668 | | 2983 |
| | | 1741 | | 3045 |
| | | 2878 | | 3085 |
| | | 3080 | | 3247 |
| | | 3340 | | |

TABLE 4

Raman spectroscopy
Peak maxima

| Modification I [cm$^{-1}$] | Modification II [cm$^{-1}$] | Modification III [cm$^{-1}$] | Hydrate [cm$^{-1}$] | NMP solvate [cm$^{-1}$] |
|---|---|---|---|---|
| 84 | 86 | 85 | 85 | 85 |
| 111 | 184 | 112 | 111 | 105 |
| 642 | 276 | 165 | 132 | 119 |
| 672 | 345 | 671 | 642 | 485 |
| 687 | 485 | 712 | 672 | 671 |
| 745 | 643 | 743 | 711 | 710 |
| 779 | 672 | 778 | 744 | 743 |
| 792 | 716 | 793 | 778 | 776 |
| 1083 | 742 | 996 | 793 | 800 |
| 1099 | 778 | 1093 | 922 | 1193 |
| 1232 | 800 | 1288 | 1073 | 1229 |
| 1280 | 864 | 1322 | 1083 | 1233 |
| 1307 | 925 | 1428 | 1097 | 1242 |
| 1325 | 995 | 1442 | 1231 | 1259 |
| 1343 | 1086 | 1475 | 1301 | 1282 |
| 1428 | 1119 | 1555 | 1325 | 1313 |
| 1473 | 1149 | 1610 | 1428 | 1319 |
| 1485 | 1196 | 1626 | 1473 | 1328 |
| 1548 | 1227 | 1663 | 1485 | 1412 |
| 1605 | 1248 | 1669 | 1548 | 1433 |
| 1638 | 1282 | 1723 | 1605 | 1473 |
| 1664 | 1310 | 2881 | 1638 | 1608 |
| 1722 | 1330 | 2992 | 1722 | 1629 |
| 2899 | 1432 | 3020 | 2885 | 1660 |
| 2944 | 1474 | 3098 | 2898 | 1763 |
| 2983 | 1556 | | 2944 | 2844 |
| 3074 | 1608 | | 2983 | 2889 |
| | 1631 | | 3074 | 2931 |
| | 1648 | | | 2946 |
| | 1722 | | | 2984 |
| | 2885 | | | 3075 |
| | 2938 | | | 3096 |
| | 2989 | | | |
| | 3077 | | | |
| | 3091 | | | |

TABLE 5

FIR spectroscopy
Peak maxima

| Modification I [cm$^{-1}$] | Modification II [cm$^{-1}$] | Hydrate [cm$^{-1}$] | NMP solvate [cm$^{-1}$] |
|---|---|---|---|
| 82 | 83 | 83 | 84 |
| 97 | 96 | 96 | 126 |
| 138 | 126 | 126 | 137 |
| 169 | 146 | 134 | 169 |
| 179 | 159 | 138 | 190 |
| 210 | 190 | 156 | 209 |
| 226 | 213 | 168 | 237 |
| 247 | 244 | 179 | 282 |
| 272 | 279 | 226 | 297 |
| 283 | 293 | 247 | 308 |
| 298 | 304 | 271 | 317 |
| 303 | 344 | 298 | 344 |
| 350 | 363 | 304 | 353 |
| 394 | 401 | 349 | 400 |
| 417 | 416 | 394 | 413 |
| 438 | 437 | 408 | 417 |
| 458 | 456 | 417 | 432 |
| 475 | 484 | 438 | 459 |
| 484 | | 455 | 471 |
| | | 472 | 485 |
| | | 484 | 498 |

TABLE 6

NIR spectroscopy
Peak maxima

| Modification I [cm$^{-1}$] | Modification II [cm$^{-1}$] | Modification III [cm$^{-1}$] | Hydrate [cm$^{-1}$] | NMP solvate [cm$^{-1}$] |
|---|---|---|---|---|
| 4082 | 4086 | 4080 | 4083 | 4040 |
| 4142 | 4228 | 4218 | 4228 | 4084 |
| 4170 | 4418 | 4329 | 4305 | 4213 |
| 4228 | 4457 | 4398 | 4384 | 4382 |
| 4299 | 4634 | 4606 | 4631 | 4552 |
| 4376 | 4905 | 4891 | 4905 | 4638 |
| 4429 | 5846 | 5066 | 5145 | 4830 |
| 4479 | 5911 | 6022 | 5760 | 5815 |
| 4633 | 6026 | 6072 | 5833 | 6091 |
| 4791 | 6081 | | 5889 | 7213 |
| 4877 | 6582 | | 6023 | 8527 |
| 4907 | | | 6076 | |
| 5081 | | | 6555 | |
| 5760 | | | 6868 | |
| 5885 | | | | |
| 6002 | | | | |
| 6441 | | | | |
| 6564 | | | | |
| 8473 | | | | |
| 8833 | | | | |

Example 7

Preparation of 5-chloro-N-({(5S)-2-oxo-3-[4-(3-oxo-4-morpholinyl)-phenyl]-1,3-oxazolidin-5-yl}-methyl)-2-thiophenecarboxamide in Amorphous Form Example 7.1

About 50 mg of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were fused on a Kofler heating bench at about 240° C. and subsequently brought to room temperature by shock cooling. The active substance was investigated by X-ray diffractometry and was present in the amorphous form.

Example 7.2

About 3 g of 5-chloro-N-({(5S)-2-oxo-3-[4-(3-oxo-4-morpholinyl)-phenyl]-1,3-oxazolidin-5-yl}-methyl)-2-thiophenecarboxamide in the modification I were fused in a drying oven at about 250° C. and subsequently brought to room temperature by shock cooling. The active compound was investigated by X-ray diffractometry and was present in the amorphous form.

TABLE 7

Differential scanning calorimetry and thermogravimetry (amorphous form)

| Glass transition temperature: | about 83° C. |
|---|---|

TABLE 8

Spectroscopy (amorphous form)
Peak maxima

| IR [cm$^{-1}$] | Raman [cm$^{-1}$] | FIR [cm$^{-1}$] | NIR [cm$^{-1}$] |
|---|---|---|---|
| 467 | 486 | 91 | 4006 |
| 512 | 642 | 97 | 4081 |
| 550 | 673 | 137 | 4224 |
| 595 | 711 | 169 | 4307 |
| 613 | 742 | 246 | 4403 |
| 643 | 781 | 272 | 4634 |
| 689 | 923 | 297 | 4875 |
| 709 | 965 | 248 | 5193 |
| 725 | 1016 | 393 | 5865 |
| 750 | 1078 | 416 | 6017 |
| 810 | 1126 | 438 | 6073 |
| 834 | 1224 | 456 | 6696 |
| 864 | 1243 | 474 | 7028 |
| 921 | 1290 | 474 | 8452 |
| 995 | 1326 | | 8873 |
| 1015 | 1428 | | |
| 1026 | 1479 | | |
| 1058 | 1548 | | |
| 1083 | 1607 | | |
| 1126 | 1642 | | |
| 1161 | 2158 | | |
| 1222 | 2975 | | |
| 1288 | 3090 | | |
| 1312 | | | |
| 1325 | | | |
| 1380 | | | |
| 1407 | | | |
| 1428 | | | |
| 1480 | | | |
| 1516 | | | |
| 1549 | | | |
| 1607 | | | |
| 1647 | | | |
| 1753 | | | |
| 2126 | | | |
| 2869 | | | |
| 2933 | | | |
| 2967 | | | |
| 3084 | | | |
| 3317 | | | |

The invention claimed is:

1. A compound of the formula (I)

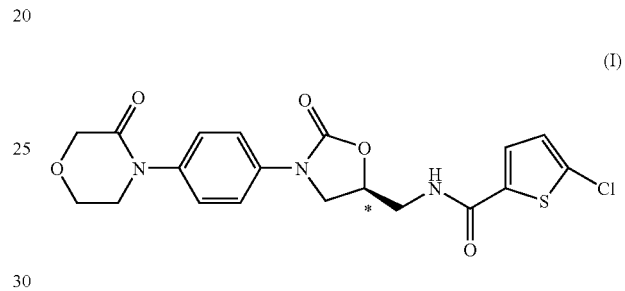

(I)

in the modification II, wherein the compound of the formula (I) in the modification II shows peak maxima in the NIR spectra at 4086, 4228, 4418, 4457, 4634, 4905, 5846, 5911, 6026, 6081 and 6582 cm$^{-1}$.

2. A process for preparing a medicament comprising combining the compound of claim 1 with an inert, nontoxic, pharmaceutically suitable excipient.

3. A medicament comprising the compound of claim 1 and an inert, nontoxic, pharmaceutically suitable excipient.

4. A medicament comprising the compound of claim 1 in combination with a further active substance.

5. The medicament of claim 4, wherein the further active substance is a lipid-lowering agent, a coronary therapeutics/vasodilator, a plasminogen activator, an anticoagulant, a substance that inhibits platelet aggregation, or a fibrinogen receptor antagonist.

* * * * *